US005850025A

United States Patent [19]
Mirkov et al.

[11] Patent Number: 5,850,025
[45] Date of Patent: Dec. 15, 1998

[54] PROTECTION OF PLANTS AGAINST PLANT PATHOGENS

[75] Inventors: Theodore Erik Mirkov, Harlingen, Tex.; Leona C. Fitzmaurice, Madison, Wis.

[73] Assignee: Sibia Neurosciences, Inc., La Jolla, Calif.

[21] Appl. No.: 919,093

[22] Filed: Apr. 22, 1997

Related U.S. Application Data

[63] Continuation of Ser. No. 373,390, Jan. 12, 1995, abandoned, which is a continuation-in-part of Ser. No. 798,223, Nov. 25, 1991, Pat. No. 5,422,108, which is a continuation-in-part of Ser. No. 762,679, Sep. 19, 1991, abandoned.

[51] Int. Cl.$^6$ .................. A01H 5/00; C12N 15/56; C12N 15/82; C12N 15/12
[52] U.S. Cl. .................. 800/279; 800/288; 800/298; 800/301; 800/317.2; 800/317.3; 800/317.4; 800/320.2; 435/69.1; 435/69.8; 435/70.1; 435/206; 435/418; 435/419; 435/421; 435/468; 536/23.5
[58] Field of Search .................. 800/205, 250, 800/255, DIG. 42–44, 57, 279, 288, 298, 301, 317.2, 317.3, 317.4, 320.2; 435/69.1, 70.1, 172.3, 418, 419, 421, 206, 69.8, 468; 536/23.5

[56] References Cited

U.S. PATENT DOCUMENTS

| | | | |
|---|---|---|---|
| 4,372,080 | 2/1983 | Rushing | 47/57.6 |
| 4,684,611 | 8/1987 | Schilperoort et al. | 435/172.3 |
| 4,895,800 | 1/1990 | Tschopp et al. | 435/69.3 |
| 4,940,835 | 7/1990 | Shah et al. | 800/205 |
| 4,940,840 | 7/1990 | Suslow et al. | 800/205 |
| 5,041,236 | 8/1991 | Carpenter et al. | 252/174.12 |
| 5,349,122 | 9/1994 | Hain et al. | 800/205 |
| 5,422,108 | 6/1995 | Mirkov et al. | 424/94.61 |
| 5,589,626 | 12/1996 | Hain et al. | 800/205 |

FOREIGN PATENT DOCUMENTS

| | | |
|---|---|---|
| 0184288 | 6/1986 | European Pat. Off. . |
| A1 0184288 | 6/1986 | European Pat. Off. . |
| 0366869 | 5/1990 | European Pat. Off. . |
| A2 0366869 | 5/1990 | European Pat. Off. . |
| A1 0412381 | 7/1990 | European Pat. Off. . |
| 0412381 | 2/1991 | European Pat. Off. . |
| 0425019 | 5/1991 | European Pat. Off. . |
| 60-215605 | 10/1985 | Japan . |
| 8900194 | 1/1989 | WIPO . |
| 8904320 | 5/1989 | WIPO . |
| 8904371 | 5/1989 | WIPO . |
| 9012866 | 11/1990 | WIPO . |
| 9305645 | 4/1993 | WIPO . |

OTHER PUBLICATIONS

Brodey, et al., Baterial blotch disease of the cultivated mushroom is caused by an ion channel forming lipodepsipeptide toxin, *Molec. Plant–Microbe Interactions*, 4(4):407–411, 1991.

Cetiner, et al., Utilizing novel lytic peptides for improving bacterial disease resistance in plants, *Hort Science*, Supplement p. 65, Meeting date: Jul. 29, 1989–Aug. 3, 1989.

Chrispeels, Sorting of proteins in the secretory system, *Ann. Rev. Plant Physiol. Plant Molec. Biol.*, 42:21–53, 1991.

Destefano–Beltran, et al., Enhancing bacterial and fungal disease resistance in plants: Application to potato, *Biotechnology in Agriculture*, Chpt. 15, pp. 205–222, 1991.

Destefano–Beltran, et al., Introduction into plants of genes which encode some of the natural components of the humoral immune response of *Hyalophora cecropia*, *Jrnl. of Cell. Biochem.*, Supp. 14E, Mar. 31–Apr. 22, 1990, 1–316.

Digan, et al., Continuous production of a novel lysozyme via secretion form the yeast *Pichia pastoris*, *Bio/Technology*, 7:160–164, 1989.

Dobson, et al., Stomach Lysozymes fo Ruminants, *J. of Biol.Chem.*, No. 18, 259:11617–11625, 1984.

Fillatti, et al., Efficient transfer of a glyphosate tolerate gene into tomato using a binary *Agrobacaterium tumefaciens* vector, *Biotechnology*, 5:726–730, 1987.

Freeman, et al., A comparison of methods for plasmid delivery into plant protoplasts, *Plant & Cell Physiol.*, No. 25, 8: 1353–1365, 1984.

Hancock, Bacterial outer membranes: Evolving concept, *ASM News*, No. 4, 57:175–182, 1991.

Hippe, et al., In situ localization of a foreign protein in transgenic plants by immunoelectron microscopy following high pressure freezing. Freeze substitution and low temperature embedding, *Eur. J. Cell Biol.*, 50:230–234, 1989.

Horsch, et al., A double filter paper technique for planting culture plant cells, In Vitro, No. 16, 2:103–108, 1980.

Hughes, et al., Perspectives in plant genetic engineering and biopharmacy, *BioPharm.*, pp. 18–28, May 1991.

Irwin, et al., Multiple cDNA sequences and the evolution of bovine stomack lysozyme, *J. Biol. Chem.*, 264:11387–11393,.

(List continued on next page.)

*Primary Examiner*—David T. Fox
*Attorney, Agent, or Firm*—Stephanie L. Seidman; Heller Ehrman White & McAuliffe

[57] ABSTRACT

Transgenic plants that express properly processed ruminant or ruminant-like lysozymes and that are resistant to bacterial pathogens, including both gram-negative and gram-positive bacteria, are provided. A preferred embodiment provides transgenic tobacco plants that express a sufficient concentration of properly processed bovine lysozyme c2 to render the plants less susceptible to bacterial plant pathogens.

Methods and compositions for treatment of plants, seeds and other plant tissues prior to or after exposure or infection with bacterial plant pathogens are also provided. In particular, compositions and methods of contacting plants with such compositions that contain a concentration of bovine lysozyme c2 or other ruminant or ruminant-like lysozyme are provided.

A signal sequence that is effective for properly processing heterologous proteins that are expressed in transgenic plants is also provided.

18 Claims, No Drawings

OTHER PUBLICATIONS

Jigami, et al., Expression of synthetic human–lysozyme gene in *Saccharomyces cerevisiae*: us of a synthetic chicken–lysozyme signal sequence for secretion and processing, *Gene*, 43:273–279, 1986.

Jolles, et al., Stomach lysozymes of ruminants, *J. of Biol. Chem.*, No. 18, 259:11617–11625, 1984.

Jung, et al., Exons encode functional and structural units of chicken lysozyme, *Proc. Natl. Acad. Sci. USA*, 77(10):5759–5763.

Krens, et al., In Vitro transformation of plant protoplasts with Ti–plasmid dNA, *Nature*, 206:72–74, 1982.

Kyozuka, et al., High frequency plant regeneration from rice protoplasts by novel nurse culture methods, *Mol. Gen. Genet.*, 206:408–413, 1987.

Lorz, et al., Gene transfer to ceereal cells mediated by protoplast transformation, *Mol. Gen. Genet.*, 199:178–182, 1985.

Lundblad, et al., Chitinase in goat serum, *Eur. J. Biochem.*, 46:367–376, 1974.

Lund, et al., Bacterial chitinase is modified and secreted in transgenic tobacco, *Plant Physiol.*, 130–135, 1989.

Malmberg, et al., Molecular biology of plants, *Mol. Biol. of Plants*, p. 88, 1985.

Pahud and Widmer, Calf rennet lysozyme, *J. Biochem.*, 201:661–664, 1982.

Potrykus, et al., Gene transfer of cereals: An assessment, *Bio/Technology*, 8:535–542, Jun. 1990.

Rhodes, et al., Genetically transformed maize plants from protoplasts, *Science*, 240:204–207 (1988).

Shields, Agricultural genetics: Towards insect–resistant plants, *Nature*, 328:12–13, 1987.

Shillito, et al., Agarose planting and bead type culture technique enable and stimulate development of protoplast–derived colonies in a number of plant species, *Plant Cell Reports*, 2:244–247, 1983.

Uchimiya, et al., Transgenic plants, *J. of Biol. Chem.*, 12:1–19, 1989.

Vakil, et al., Susceptibility of several microorganisms to milk lysozymes, *J. Dairy Science*, 52:1192–1197, Mar. 18, 1969.

Enzymes: mechanism, structure, and regulation, *The Molec. Comp. of Cells*, pp. 231–310.

Jieng et al. 1980. Proc. Natl. Acad. Sci. USA 77(10):5759–63.

Cetiner et al. 1989. Hart Science, Supplement p. 65, Meeting date Jul. 29, 1989–Aug. 3, 1989.

Bacterial outer membranes: evolving concepts Hancock, *ASM News*, No. 4, 57:175–182, 1991.

Stomach Lysozymes of Ruminants Dobson, et al., *J. of Biol. Chem.*, No. 18, 259:11607–11616, 1984.

Stomach Lysozymes of Ruminants Jolles, et al., *J. of Biol. Chem.*, No. 18, 259:11617–11625, 1984.

Transgenic Plants Uchimiya, et al., *J. of Biotech.*, 12:1–19, 1989.

A comparison of methods for plasmid delivery into plant photoplasts Freeman, et al., *Plant & Cell Physiol.*, No. 25 8:1353–1365, 1984.

Gene transfer to ceereal cells mediated by protoplast transformation Lorz, et al., *Mol. Gen. Genet.*, 199:178–182, 1985.

In vitro transformation of plant protoplasts with Ti–plasmid DNA Krens, et al., *Nature* 296:72–74, 1982.

Perspectives in plant genetic engineering and biopharmacy Hughes, et al., *BioPharm.*, pp. 18–28, May 1991.

High frequency plant regeneration from rice protoplasts by novel nurse culture methods Kyozuka, et al., *Mol. Gen. Genet.*, 206:408–413, 1987.

A double filter paper technique for plating culture plant cells Horsch, et al., In Vitro, No. 16, 2:103–108, 1980.

Agarose planting and bead type cuture technique enable and stimulate development of protoplast–derived colonies in a number of plant species Shillito, et al., *Plant Cell Reports*, 2:244–247, 1983.

Efficient transfer of a glyphosate tolerance gene into tomato using a binary *agrobacterium tumefaciens* vector Fillatti, et al., *Biotechnology*, 5:726–730, 1987.

Sorting of proteins in the secretory system Chrispeels, *Ann. Rev. Plant Physiol. Plant Molec. Biol.*, 42:21–53, 1991.

Susceptibility of Several Microorganisms to Milk Lysozymes Vakil, et al., *J. Dairy Science*, 52:1192–1197, Mar. 18, 1969.

The Molecular and Cellular Biology of the Potato Vayda and Park, *Biotechnology in Agriculture*, 3:3 pgs.

Enhancing Bacterial and Fungal Disease Resistance in Plants: Application to Potato, Destefano–Beltran, et al., *Biotechnology in Agriculture*, Chptr 15, pp. 205–222, 1991.

Introduction into Plants Of Genes Which Encode Some Of The Natural Components Of the Humoral Immune Response of *Hyalophora Cecropia* Destefano–Beltran, et al., *Jrnl. of Cell. Biochem.*, Supp. 14E 1 pg. Mar. 31–Apr. 22, 1990.

Continuous production of a novel lysozyme via secretion from the yeast *Pichia pastoris* Digan, et al., *Bio/Technology*, 7:160–164, 1989.

Database WPI M. Nagahama, *Derwent Publications, LTD.*, Week 8612, 1 pg. (abstract) Oct. 29, 1985.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 964 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 25..459

( x i ) SEQUENCE DESCRIPTION: SEQ ID NO:1:

```
GAATTCATGT CTTACGGTCA AGGG GCT CTC GTT ATT CTG GGG TTT CTC TTC        51
```

|     |     |     |     |     |     |     | Ala | Leu | Val | Ile | Leu | Gly | Phe | Leu | Phe |     |
|-----|-----|-----|-----|-----|-----|-----|-----|-----|-----|-----|-----|-----|-----|-----|-----|-----|
|     |     |     |     |     |     |     |  1  |     |     |     |  5  |     |     |     |     |     |
| CTT | TCT | GTC | GCT | GTC | CAA | GGC | AAG | GTC | TTT | GAG | AGA | TGT | GAG | CTT | GCC | 99  |
| Leu | Ser | Val | Ala | Val | Gln | Gly | Lys | Val | Phe | Glu | Arg | Cys | Glu | Leu | Ala |     |
| 10  |     |     |     |     | 15  |     |     |     |     | 20  |     |     |     |     | 25  |     |
| AGA | ACT | CTG | AAG | AAA | CTT | GGA | CTG | GAC | GGC | TAT | AAG | GGA | GTC | AGC | CTG | 147 |
| Arg | Thr | Leu | Lys | Lys | Leu | Gly | Leu | Asp | Gly | Tyr | Lys | Gly | Val | Ser | Leu |     |
|     |     |     |     | 30  |     |     |     |     | 35  |     |     |     |     | 40  |     |     |
| GCA | AAC | TGG | TTG | TGT | TTG | ACC | AAA | TGG | GAA | AGC | AGT | TAT | AAC | ACA | AAA | 195 |
| Ala | Asn | Trp | Leu | Cys | Leu | Thr | Lys | Trp | Glu | Ser | Ser | Tyr | Asn | Thr | Lys |     |
|     |     |     | 45  |     |     |     |     | 50  |     |     |     |     | 55  |     |     |     |
| GCT | ACA | AAC | TAC | AAT | CCT | AGC | AGT | GAA | AGC | ACT | GAT | TAT | GGG | ATA | TTT | 243 |
| Ala | Thr | Asn | Tyr | Asn | Pro | Ser | Ser | Glu | Ser | Thr | Asp | Tyr | Gly | Ile | Phe |     |
|     |     | 60  |     |     |     |     | 65  |     |     |     |     | 70  |     |     |     |     |
| CAG | ATC | AAC | AGC | AAA | TGG | TGG | TGT | AAT | GAT | GGC | AAA | ACC | CCT | AAT | GCA | 291 |
| Gln | Ile | Asn | Ser | Lys | Trp | Trp | Cys | Asn | Asp | Gly | Lys | Thr | Pro | Asn | Ala |     |
|     | 75  |     |     |     |     | 80  |     |     |     |     | 85  |     |     |     |     |     |
| GTT | GAC | GGC | TGT | CAT | GTA | TCC | TGC | AGC | GAA | TTA | ATG | GAA | AAT | GAC | ATC | 339 |
| Val | Asp | Gly | Cys | His | Val | Ser | Cys | Ser | Glu | Leu | Met | Glu | Asn | Asp | Ile |     |
| 90  |     |     |     |     | 95  |     |     |     |     | 100 |     |     |     |     | 105 |     |
| GCT | AAA | GCT | GTA | GCG | TGT | GCA | AAG | CAT | ATT | GTC | AGT | GAG | CAA | GGC | ATT | 387 |
| Ala | Lys | Ala | Val | Ala | Cys | Ala | Lys | His | Ile | Val | Ser | Glu | Gln | Gly | Ile |     |
|     |     |     |     | 110 |     |     |     |     | 115 |     |     |     |     | 120 |     |     |
| ACA | GCC | TGG | GTG | GCA | TGG | AAA | AGT | CAT | TGT | CGA | GAC | CAT | GAC | GTC | AGC | 435 |
| Thr | Ala | Trp | Val | Ala | Trp | Lys | Ser | His | Cys | Arg | Asp | His | Asp | Val | Ser |     |
|     |     |     | 125 |     |     |     |     | 130 |     |     |     |     | 135 |     |     |     |
| AGT | TAC | GTT | GAG | GGT | TGC | ACC | CTG | TAACTGTGGA | GTTATCATTC | TTCAGCTCAT |  |  |  |  |  | 489 |
| Ser | Tyr | Val | Glu | Gly | Cys | Thr | Leu |     |     |     |     |     |     |     |     |     |
|     |     | 140 |     |     |     |     | 145 |     |     |     |     |     |     |     |     |     |

| TTTATCTCTT | TTTCATATTA | AGGAAGTGAT | AGTTGAATGA | AAGTTTATAC | CACCATTGTT | 549 |
| TCAAACAAAT | AACATTTTTA | CAGAAGCAGG | AGCATGTGGT | CTTTCTTCTA | AGAAGCCTAA | 609 |
| TGTTTATCTA | ATGTGTTAAT | TGTTTGATAT | TAGGCCTACA | ATATTTTTCA | GTTTGCTAAT | 669 |
| GAAACTAATC | CTGGTGAATA | TTTGTCTAAA | CTCTTAATTA | TCAAATATGT | CTCCAGTACA | 729 |
| TTCAGTTCTT | AATTAAAGCA | AGATCATTTA | TGTGCCTTGC | TGATCATGAA | GGAATATAAA | 789 |
| GAGGGATTAG | ATGAGCTGTT | TCTTTTCCTT | AATTTTATTA | GCATAGATTC | ATGCATTATG | 849 |
| ACCAAATTTA | GAGGCAGATA | AGTATTGAAA | TAACTAACCA | CAGATATGAA | ATTATGCATG | 909 |
| CTGTAAAAAA | TACAAACATT | TTCATTAAAG | GCCCTTGACC | GTAAGACATG | AATTC | 964 |

( 2 ) INFORMATION FOR SEQ ID NO:2:

( i ) SEQUENCE CHARACTERISTICS:
        ( A ) LENGTH: 145 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ala | Leu | Val | Ile | Leu | Gly | Phe | Leu | Phe | Leu | Ser | Val | Ala | Val | Gln | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Lys | Val | Phe | Glu | Arg | Cys | Glu | Leu | Ala | Arg | Thr | Leu | Lys | Lys | Leu | Gly |
|     |     |     | 20  |     |     |     |     | 25  |     |     |     |     | 30  |     |     |
| Leu | Asp | Gly | Tyr | Lys | Gly | Val | Ser | Leu | Ala | Asn | Trp | Leu | Cys | Leu | Thr |
|     |     | 35  |     |     |     |     | 40  |     |     |     |     | 45  |     |     |     |
| Lys | Trp | Glu | Ser | Ser | Tyr | Asn | Thr | Lys | Ala | Thr | Asn | Tyr | Asn | Pro | Ser |
|     | 50  |     |     |     |     | 55  |     |     |     |     | 60  |     |     |     |     |
| Ser | Glu | Ser | Thr | Asp | Tyr | Gly | Ile | Phe | Gln | Ile | Asn | Ser | Lys | Trp | Trp |

-continued

```
            65                      70                      75                      80
Cys Asn Asp Gly Lys Thr Pro Asn Ala Val Asp Gly Cys His Val Ser
                85                      90                      95
Cys Ser Glu Leu Met Glu Asn Asp Ile Ala Lys Ala Val Ala Cys Ala
                100                     105                     110
Lys His Ile Val Ser Glu Gln Gly Ile Thr Ala Trp Val Ala Trp Lys
                115                     120                     125
Ser His Cys Arg Asp His Asp Val Ser Ser Tyr Val Glu Gly Cys Thr
    130                     135                     140
Leu
145
```

(2) INFORMATION FOR SEQ ID NO:3:

(i) SEQUENCE CHARACTERISTICS:
        (A) LENGTH: 18 amino acids
        (B) TYPE: amino acid
        (D) TOPOLOGY: unknown (ii) MOLECULE TYPE: peptide (ix) FEATURE:
        (A) NAME/KEY: Peptide
        (B) LOCATION: 1..18

(xi) SEQUENCE DESCRIPTION: SEQ ID NO:3:

```
Met Lys Ala Leu Val Ile Leu Gly Phe Leu Phe Leu Ser Val Ala Val
1                   5                   10                  15
Gln Gly
```

PROTECTION OF PLANTS AGAINST PLANT PATHOGENS

RELATED APPLICATIONS

This application is a continuation of U.S. application Ser. No. 08/373,390, filed Jan. 12, 1995, now abandoned, which is a continuation-in-part of U.S. application Ser. No. 07/798,223, filed Nov. 21, 1991 and, now U.S. Pat. No. 5,422,108, which is a continuation-in-part of U.S. application Ser. No. 07/762,679, filed Sep. 19, 1991, now abandoned. Additionally, the subject matter of this application is related to U.S. application Ser. No. 07/265,634, to Digan et al., filed Nov. 1, 1988, "PRODUCTION OF ANIMAL LYSOZYME c VIA SECRETION FROM *Pichia pastoris* AND COMPOSITION THEREFOR", now abandoned, which is a continuation-in-part of U.S. application Ser. No. 07/115,940, filed Nov. 2, 1987, now abandoned. U.S. application Ser. Nos. 07/265,634 and 07/115,940 are incorporated herein in their entirety by reference thereto.

FIELD OF INVENTION

This invention is directed to transgenic plants that include heterologous DNA that encodes a ruminant lysozyme, that is expressed in the plant and that thereby provides protection against diseases caused by plant pathogens, particularly plant bacterial pathogens. This invention is also directed to seeds that are coated with a composition that contains a ruminant lysozyme and to methods of treating plants, cut flowers, fruits, seeds and other plant tissues, which are infected with one or more plant pathogens or which are susceptible to such infection, by contacting the plants, flowers, fruits or seeds with a ruminant lysozyme in order to treat them for diseases caused by plant pathogens or to make them less susceptible or resistant to diseases caused by plant pathogens. This invention is also directed to methods for producing a ruminant lysozyme from transgenic plants that express the lysozyme and to peptides that direct proper processing of heterologous proteins in transgenic plants.

BACKGROUND OF THE INVENTION

Plant Pathogens.

Plants are exposed to numerous denizens of their environment, including bacteria, viruses, fungi and nematodes. Although many of the interactions between these organisms and plants, particularly via the roots of the plants, are beneficial, many of the interactions are harmful to the plants. The decimation of agricultural crops, ornamental plants and other plants by diseases caused by plant pathogens, particularly bacterial pathogens, is a worldwide problem that has enormous economic impact.

There are many pathogenic species of bacteria, fungi and nematodes. Fungal plant pathogens include species from the genera Fusarium, Pythium, Phytophthora, Verticillium, Rhizoctonia, Macrophomina, and others (see, e.g., U.S. Pat. No. 4,940,840 to Suslow et al.). Diseases caused by such fungal species include pre- and post-emergence seedling damping-off, hypocotyl rots, root rots, crown rots, and others. Nematode pathogens, which include species from the genera *Meloidogyne heterodera*, and others, cause diseases such as root galls, root rot, stunting and various other rots. In addition, nematodes serve as vectors for viral plant pathogens.

Bacterial pathogens have a significant impact on worldwide agriculture. Such pathogens include species of Pseudomonas, Erwinia, Agrobacteria, Xanthomonas, Clavibacter and others. Pseudomonas and Xanthomonas species affect a large number of different crops. For example, *Pseudomonas tolaasii* Paine, which causes brown blotch disease of the cultivated mushroom *Agaricus bisporus* (Lange) Imbach, produces an extracellular toxin, tolaasin, which disrupts membranes of fungal, bacterial, plant and animal cells; *Pseudomonas syringae* pv. *tomato* causes bacterial speck on tomato; *Xanthomonas campestris* pv. *malvacearum* causes angular leaf spot on cotton; and *Pseudomonas solanacearum* causes bacterial wilt on potatoes. Potatoes are also susceptible to post-harvest soft rot diseases caused by *Erwinia carotovora*. Such post-harvest soft rot diseases caused by *Erwinia carotovora* subsp. *carotovora* have a substantial impact on the potato industry.

Agricultural production of major crops has always been impeded by plant pathogens. Often diseases caused by plant pathogens limit the growth of certain crops in specific geographical locations and can destroy entire crops. Crop losses resulting from the deleterious effects of plant pathogens are, thus, a serious worldwide agricultural problem, particularly since there are no known treatments for many of the diseases caused by plant pathogens. Even in instances in which agrichemicals and pesticides are effective, their use is increasingly under attack because of the deleterious effects on the environment and on those who handle such products.

Because pesticides are often ineffective, unavailable and environmentally unacceptable, there is a need to develop alternative means for effectively eradicating or reducing the harmful effects of plant pathogens. In recent years, research has focused on the development of means for biocontrol of such pathogens and on the development of pathogen-resistant plants by breeding or by genetic engineering. There are, however, few reports of successful production of disease-resistant plants.

U.S. Pat. No. 4,940,840 to Suslow et al., however, describes the production of recombinant strains of Rhizobacterium that express heterologous DNA encoding the bacterial enzyme chitinase, which degrades chitin. Chitin is an unbranched polysaccharide polymer that contains N-acetyl-D-glucosamine units and occurs as an integral part of the cell walls of fungi and the outer covering of nematodes, nematode eggs and nematode cysts. The chitinase-expressing bacteria are applied to the plants or to soil as a means for inhibiting the growth of chitinase-sensitive fungi and nematodes. U.S. Pat. No. 4,940,840 also describes the production of transgenic tobacco plants that express chitinase and that appear to express sufficient levels of chitinase to inhibit the growth of fungal pathogens and are thereby less susceptible to diseases caused by such pathogens. Bacterial pathogens, however, do not have chitinous cell walls and are not inhibited by chitinase.

Bacterial Cell Walls.

Bacterial cell walls are composed of peptidoglycan, which is a polysaccharide that contains amino sugars that are covalently crosslinked via small peptide bridges. The basic recurring unit in the peptidoglycan structure is the muropeptide, which is a disaccharide of N-acetyl-D-glycosamine and N-acetylmuramic acid in β(1–4) linkage. Tetrapeptide side chains, containing L-alanine, D-glutamic acid or D-glutamine, and either meso-diaminopimelic acid, L-lysine, L-hydroxylysine or ornithine, are attached to the carboxyl group of the N-acetylmuramic acid residues. The parallel polysaccharide chains are cross-linked through their peptide side chains. The terminal D-alanine residue of the side chain of one polysaccharide chain is joined covalently with the peptide side chain of an adjacent polysaccharide chain, either directly as in *Escherichia coli* (*E. coli*), or through a short connecting peptide as in *Staphylococcus*

*aureus*. The peptidoglycan forms a completely continuous covalent structure around the cell.

The cell walls of both gram-positive and gram-negative bacteria include a peptidoglycan backbone. Gram-positive bacteria possess cell walls that contain multilayered peptidoglycan and are encased in up to 20 layers of cross-linked peptidoglycan. Gram-negative bacteria have cell walls that contain mono or bilayered peptidoglycan and are more complex than the cell walls of gram-positive bacteria. Gram-negative and gram-positive bacteria also differ in accessory components, which are attached to the peptidoglycan backbone. The accessory components include polypeptides, lipoproteins and complex lipopolysaccharide (LPS), which form an outer lipid membrane surrounding the peptidoglycan skeleton. In particular, the cell walls of gram-negative bacteria contain a very complex lipopolysaccharide, which forms an outer membrane that provides gram-negative bacteria with a unique barrier that reportedly functions to selectively exclude environmental molecules, including lysozyme (Hancock, R. E. W. (1991) *ASM News* 57:175–182).

Lysozymes.

The peptidoglycan backbone of the bacterial cell wall is resistant to peptide-hydrolyzing enzymes, which do not cleave peptides that contain D-amino acids, but can be cleaved by lysozymes. Lysozymes are a ubiquitous family of enzymes that occur in many tissues and secretions of humans, other vertebrates and invertebrates, as well as in plants, bacteria and phage. Lysozymes, which are 1,4-β-N-acetylmuramidases, are basic enzymes that catalyze the hydrolysis of the β-(1–4)glycosidic bond between the C-1 of N-acetylmuramic acid and the C-4 of N-acetylglucosamine, which occurs in the component of bacterial cell walls, bacterial peptidoglycan or murein. Some lysozymes also display a more or less pronounced chitinase activity, corresponding to a random hydrolysis of 1,4-β-N-acetylglucosamine linkages in chitin. A slight esterase activity of lysozymes has also been reported.

Types of lysozymes.

Several different types of lysozymes, based upon their amino acid sequence and structure, have been identified.

Lysozymes of the c, or "chicken", type contain 129–130 amino acids in their mature, secreted forms. About 40 of the 129–130 amino acids appear to be invariant among different species. Two of the several carboxyl groups of the type c lysozymes, which correspond to the Glu-35 and Asp-52 of the chicken egg white lysozyme, occur in similar positions in all c-type lysozymes. These groups are essential for lysozyme activity. A third carboxyl group, which corresponds to Asp-101 in chicken egg white lysozyme, is involved in a substrate binding interaction, and occurs in most c-type lysozymes. The eight half-cysteine residues of all of the c-type lysozymes are invariant. The disulfide bonds formed by the cysteines play an important role in the formation and maintenance of the secondary and tertiary structures of the lysozymes, which appear to be similar for all type c lysozymes.

The complete primary structures are known for the mature lysozyme c from numerous sources, including (1) hen egg white, quail, turkey, guinea fowl, duck and pheasant; (2) human milk and urine; (3) moth; (4) baboon; (5) rat; and (6) bovine stomach. The sequence of DNA that encodes mature human milk lysozyme c is also known. See European Patent Application Publication Nos. 0 181 634, 0 208 472, and 0 222 366.

The g-type lysozymes contain about 185 amino acids in their mature forms, exhibit low activity on N-acetylglucosamine polymers, and do not cross-react immunologically with lysozymes of the c-type. Lysozymes of the g-type have an unusually high occurrence of paired amino acids, in which the same amino acid occurs at neighboring positions in the molecules, and all of the four half-cysteine residues in the g-type molecules are situated in the N-terminal half of the chain. C-type lysozymes are equally active on peptide-substituted or unsubstituted peptidoglycan and are also active on chitin oligosaccharides. G-type lysozymes, which have activity against the linear peptidoglycan similar to that of the c-type enzymes, do not act on chitin oligosaccharides. Furthermore, g-type enzymes act only as hydrolases, whereas, c-type lysozymes are capable of both hydrolysis and transglycosylation.

The existence of other distinct types of lysozymes, which differ from the c and g types on the basis of structural, catalytic and immunological criteria, has also been reported. Bacteriophage lysozymes, such as T2 and T4 phage lysozymes, include 164 amino acids and have a molecular weight of 18,700. A lysozyme activity has been detected in several plant tissues, but the plant lysozyme appears to act as a chitinase rather than as a 1,4-β-N-acetylmuramidase.

In addition, lysozymes may also be characterized on the basis of their in vivo biological activity. Because of their ability to cleave the peptidoglycan bacterial cell wall, some lysozymes are involved in mammalian defense systems. In addition, since lysozymes also possess the ability to indirectly stimulate the production of antibodies against a variety of antigens, such enzymes may also be employed to enhance resistance against infection. Lysozymes may also have anti-tumor activity.

A number of mammalian species, which have a foregut or rumen, have an unusually high level of lysozyme in the fundic region (anterior part) of the abomasum (stomach). This lysozyme, which has a unique activity profile, appears to have evolved to perform functions distinct from other lysozymes. Most lysozymes appear to function to protect against infection and in other defense systems. Ruminant stomach lysozymes, however, have evolved as digestive enzymes to digest the microbes that grow in the foregut and thereby scavenge the nutrients used by these microbes that digest cellulose.

Ruminant gut lysozymes.

A ruminant is a cud-chewing mammal with two stomachs: a foregut in which anaerobic gram-positive bacteria digest cellulose, thereby permitting the ruminant to use cellulose as a source of energy and nutrients; and a true stomach. Ruminants, such as domestic cattle and other cud-chewing mammals in the order Artiodactyla have developed a symbiotic relationship with bacteria that live in the rumen thereby permitting ruminants to use cellulose as a major nutrient. The bacteria digest cellulose and other dietary components and rapidly grow and divide to large numbers. They convert a significant percentage of the nutrients that are ingested by the ruminant. The bacteria then enter the fundic region of the stomach.

Cell walls of the bacterial cells are digested only slowly by the normal repertoire of enzymes that are present in the mammalian gut, but, concomitant with the evolution of the symbiotic relationship with microbes, lysozymes that digest the cell walls of the microbes under the acidic conditions in the true stomach of ruminants and ruminant-like species, including cows, sheep and deer, have evolved (Dobson et al. (1984) *J. Biol. Chem.* 259:11607–11616). The lysozymes digest the bacteria, thereby enabling the ruminant to utilize the lysed bacteria as a source of carbon, nitrogen, and phosphorus for energy and growth.

Bovine stomach lysozyme was first purified from abomasum mucosa by Dobson et al. ((1984) *J. Biol. Chem.* 259:11607–11616). Three distinct, related, non-allelic forms of lysozyme c were isolated. The three forms of lysozyme constitute approximately 10% of the total protein that can be extracted from the abomasum mucosa. These three nonallelic lysozymes, designated c1, c2 and c3, are closely related to one another antigenically and in amino acid composition. These type c lysozymes have functionally diverged from other mammalian lysozymes in that (1) the pH optimum for their enzymatic activity is approximately 5, rather than 7 as exhibited by other type c lysozymes; and (2) the type c lysozymes present in bovine abomasum are more stable in acidic environments, such as that of the abomasum, and are more resistant to proteolytic enzymes, such as pepsin, which occur in the abomasum, than other type c lysozymes (see, Jolles et al. (1984) *J. Biol. Chem.* 259:11617–11625). In addition, the complete 129 amino acid sequence of a mature bovine lysozyme c2 and the observation that antibodies prepared against the stomach lysozyme do not cross-react with non-digestive lysozymes from other tissues and secretions indicate that this enzyme appears to have diverged from other lysozymes (Jolles (1984) *J. Biol. Chem.*, 259:11617–11625).

Ruminant lysozyme c, thus, is a digestive enzyme that lyses foregut gram-positive bacteria in the stomach and the proximal part of the small intestine, which permits ruminants to use the lysed bacteria as sources of carbon, nitrogen and phosphorous. This lysozyme is confined to the stomach; it has not been found in other tissues or secretions. In non-ruminant species, stomach lysozymes appear to be identical with the lysozymes in other tissues and secretions.

Lysozymes as anti-bacterial agents.

Lysozymes are known to exhibit anti-bacterial activity and activity against other pathogens, such as nematodes, that contain chitin. In addition, when used as antimicrobial agents, lysozymes are generally employed in combination with other agents, such as lacto-transferrin, complement, antibodies, vitamins, other enzymes and various antibiotics, including tetracycline and bacitracin. Such antimicrobial compositions are used as preservatives for foods, such as cheese, sausage and marine products, as ripening agents for cheese, and also in skin, hair care and other cosmetic compositions.

Antimicrobial compositions that contain ruminant lysozyme c and endo-β-N-acetylglucosaminidase or endoglycopeptidase that are formulated as mouthwashes, soaps, contact lens cleaners and other similar products are described in European Patent Application 0 42 019 A1 (Feb. 5, 1991, THE PROCTOR & GAMBLE COMPANY). These compositions include the endo-β-N-acetylglucosaminidase or endoglycopeptidase in addition to the lysozyme because the lysozyme c is not sufficiently effective against bacteria, such as *Staphylococcus aureus*, that occur on the skin, and in the mouth and eyes, to be used alone.

In addition, lysozymes are purportedly not effective against gram-negative bacteria (see, European Patent Application 0 42 019 A1, Feb. 5, 1991, THE PROCTOR & GAMBLE COMPANY). As discussed above, gram-negative bacteria are encased in a lipopolysaccharide (LPS) outer membrane, which reportedly functions to exclude environmental molecules, including lysozyme (Hancock, R. E. W. (1991) *ASM News* 57:175–182).

Thus, lysozyme appears to be most useful, when used as an antimicrobial agent, for lysing gram-positive bacteria. It would not appear that lysozyme is the agent of choice for organisms such as plants that are plagued by diseases caused by gram-negative organisms.

The majority of bacterial plant pathogens, about 95%, including *Agrobacterium tumefaciens, Pseudomonas syringae, Xanthomonas campestris* and *Erwinia carotovora*, are gram-negative. In addition, as described in the examples below, lysozymes, such as chicken lysozyme, are unstable, particularly under conditions in which plants are grown or under which seeds are stored. Therefore, it would appear that lysozymes are unsuitable for treating plants, since most bacterial pathogens are gram-negative and lysozymes are too unstable to protect against infection for sufficient time to be effective.

Control of plant pathogens.

There are few effective treatments or means for preventing plant diseases of bacterial origin or for controlling plant bacterial pathogens. The treatments that are used are often environmentally unsound and generally do not have systemic or prophylactic activity. Pesticides, including heavy metal-containing sprays and antibiotics, such as streptomycin, are no longer considered environmentally acceptable and are often ineffective. For example, *Pseudomonas syringae* pv. *tomato*, which causes bacterial speck on tomato, is presently controlled by frequent application of copper-containing sprays, which, in addition to their unfavorable environmental impact, select for copper-resistant strains. Treatment of apple and pear orchards with streptomycin in order to control the blight pathogen, *Erwinia amylovora*, has resulted in the appearance of streptomycin-resistant strains. *Xanthomonas campestris* pv. *malvacearum*, which causes angular leaf spot on cotton, presently is only controlled by treating seeds with mercury-containing compounds and copper sprays. Other *Xanthomonas campestris* species, such as *X. campestris* pv. *vesicatoria* and *X. campestris* pv. *campestris*, can be seedborne, and there are no effective means for treating the seeds without injury.

Since there are few means for controlling plant bacterial pathogens, and those that are available, such as heavy metal-containing sprays and antibiotics, are not highly effective and are environmentally unacceptable, and since there are relatively few bacterial pathogen-resistant vegetable or fruit plants available, there is a need for the development of effective, non-toxic, biodegradable and environmentally acceptable means for the control of plant pathogens. There is also a need to develop disease-resistant plants and to develop means for treating plants to eradicate or control plant diseases of bacterial origin.

Therefore, it is an object of this invention to provide methods for treating plants, plant tissues, and seeds infected with plant pathogens and for treating non-infected plants to render them resistant to or less susceptible to infection by plant pathogens.

It is another object to provide methods for disinfecting seeds to render the seeds and resulting plants free from infection by common plant pathogens.

It is a further object to provide transgenic plants that are resistant to or less susceptible to infection by a variety of plant pathogens.

It is also an object to provide transgenic plants that express and properly process the product of a heterologous gene that encodes an agent that effectively inhibits the growth of or eradicates a variety of plant pathogens, and to provide a means for effecting the proper processing of the heterologous gene product.

SUMMARY OF THE INVENTION

Transgenic plants that are resistant to or are less susceptible to diseases caused by plant pathogens are provided. In particular, transgenic plants, including crop plants, such as tobacco, tomato, potato, rice, corn, cotton and others, that express heterologous DNA that encodes a ruminant lysozyme or other unusually stable lysozyme and that are thereby rendered resistant or less susceptible to diseases caused by plant pathogens, particularly common bacterial pathogens, such as species of Pseudomonas, Agrobacterium, Xanthomonas, Erwinia and Clavibacter, are provided. In preferred embodiments, transgenic plants that express DNA that encodes bovine lysozyme c are provided.

Methods for protecting plants against infection by bacterial pathogens in which the plants are contacted with a composition that contains an effective concentration of a lysozyme that is sufficiently stable to protect the plant against infection by such pathogens are provided. In particular, methods in which an effective amount of a ruminant lysozyme, ruminant-like lysozyme or mixture thereof is sprayed on crop plants in the field or in a greenhouse are provided. In preferred embodiments, a composition that contains bovine lysozyme c is sprayed on the crop plant. In addition, methods are provided in which ruminant lysozymes are sprayed on cut flowers and/or are included in the water in which the cut flowers are displayed at a concentration and in an amount that is effective to inhibit bacterial growth during transport, storage and display of the cut flowers. Methods are also provided for disinfecting seeds by contacting them or coating them with compositions that contain ruminant or ruminant-like lysozymes. Seeds that are coated with compositions that contain such lysozymes are also provided.

Compositions formulated for spraying on plants, or otherwise contacting plants, that contain concentrations of bovine lysozyme c that are effective for inhibiting the growth of plant pathogens in and on susceptible plants, for treating infected plants or for rendering uninfected plants resistant to infection are also provided.

Methods for producing ruminant and ruminant-like lysozyme by developing transgenic plants that express and properly process the respective lysozyme, planting, growing, then harvesting the transgenic plants and isolating the lysozyme from the plants are provided. Finally, a signal sequence that effects proper processing of heterologous genes in transgenic plants and method for producing authentically processed heterologous proteins by growing transgenic plants are also provided. In preferred embodiments, the DNA encoding the bovine lysozyme c signal peptide, which is set forth in Sequence ID No. 3 and which is effective for directing proper processing of bovine lysozyme c2 in transgenic plants, is linked to DNA encoding other proteins and introduced into plants in order to produce properly processed proteins that are encoded by the heterologous DNA.

As described herein, ruminant and ruminant-like lysozymes exhibit unusually high stability and also sufficient activity against gram-negative plant pathogens to be useful as agents for rendering plants less susceptible or resistant to a broad spectrum of plant pathogens, including gram-negative bacteria, as well as gram-positive bacteria, or for treating plants, plant tissues, and seeds infected with such pathogens.

Transgenic plants that express DNA that encodes a ruminant or ruminant-like lysozyme and that are resistant to infection by certain microbes are produced. Such plants include, but are not limited to, tomato, potato, rice, tobacco and other crop plants. In preferred embodiments, transgenic tobacco plants that express sufficient concentrations of bovine lysozyme c to inhibit the growth of plant bacterial pathogens have been developed.

The transgenic tobacco, tomato and potato plants, which include DNA encoding bovine lysozyme c in their genomes, have been prepared by introducing DNA encoding the precursor of bovine lysozyme c, which includes the native signal sequence, into the genomes of plants using Agrobacterium Ti plasmid-based procedures.

The transgenic tobacco plants appear to express sufficient concentrations of mature, properly processed, bovine lysozyme c to render them less susceptible to plant bacterial pathogens, including gram-negative bacterial pathogens.

In addition, application of a ruminant or ruminant-like lysozyme, such as bovine lysozyme c, to plants, seeds, cut flowers and other plant tissues can effectively eradicate or reduce disease symptoms caused by plant bacterial pathogens. In preferred embodiments, bovine lysozyme c is sprayed on susceptible plants, before or after exposure to a bacterial pathogen, and thereby decreases the number of lesions formed on the plant compared to the number of lesions that would have developed in the absence of this treatment. In other preferred embodiments, seeds are contacted with a composition containing bovine lysozyme c for the purpose of eradicating bacterial pathogens with which they are infected or to which they are susceptible.

DESCRIPTION OF THE PREFERRED EMBODIMENTS

Definitions.

Unless defined otherwise, all technical and scientific terms used herein have the same meaning as is commonly understood by one of skill in the art to which this invention belongs. All publications mentioned herein are incorporated by reference thereto. All U.S. patents mentioned herein are incorporated in their entirety by reference thereto.

The amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, ruminant and ruminant-like lysozyme refers to lysozymes that occur in the abomasum of ruminants, such as cows, and ruminant-like animals, such as sheep, goats and deer. Ruminant and ruminant-like lysozymes also exhibit substantial lytic activity centered at pH 5, rather than around pH 7 as exhibited by other lysozymes. They also exhibit more resistance to proteolytic enzymes, such as pepsin, which occur in the abomasum, as compared to other lysozymes, such as hen egg white (chicken) lysozyme c. Ruminant and ruminant-like lysozymes also refers to any other lysozymes that exhibit the following properties: 1) substantial lytic activity against gram-negative bacteria, such as *Erwinia carotovora*, compared to other lysozymes which exhibit little or no activity against gram-negative bacteria; 2) lytic activity against gram-positive bacteria, such as *Micrococcus luteus*; and 3) substantially more stability at room temperature than other lysozymes, such as hen egg white lysozyme. Bovine lysozyme c is a preferred lysozyme for use herein.

As used herein, ruminant and ruminant-like lysozyme also encompasses lysozymes that are encoded by altered or variant forms of DNA encoding ruminant lysozyme or other proteins that are basic enzymes that catalyze the hydrolysis of the $\beta$-(1–4)glycosidic bond between the C-1 of N-acetylmuramic acid and the C-4 of N-acetylglucosamine, that have the ability to inhibit the growth of or lyse gram-negative, as well as gram-positive, bacteria, and that are more stable than hen egg white lysozyme at room temperature. Lysozymes that exhibit substantially the same catalytic or enzymatic properties and that are otherwise indistinguishable, other than by DNA or protein sequence, from ruminant or ruminant-like lysozymes are encompassed within the scope of lysozymes intended for use herein. Such lysozymes may be characterized on the basis of their ability to lyse gram-negative bacteria to a greater extent than hen egg white lysozyme and on the basis of their greater stability than hen egg white lysozyme.

The lysozyme used herein may be obtained by any method known to those of skill in the art, including isolation from mammalian or other tissue, by isolation of protein produced upon expression of cloned or synthetic DNA in a selected host cell in vitro, or by chemical synthesis of a protein that exhibits the activities and properties of a ruminant lysozyme. Bovine lysozyme c produced in *P. pastoris* as described in U.S. patent application Ser. No. 07/265,634, to Digan et al., now abandoned, or a lysozyme that has an amino acid sequence substantially the same as that set forth in Sequence ID No. 1 below is the preferred lysozyme for use herein.

As used herein, biological activity of a lysozyme refers to the ability of a particular protein to catalyze the hydrolysis or other cleavage of the β-(1–4)glycosidic bond between the C-1 of N-aceytlmuramic acid and the C-4 of N-acetylglucosamine. Such activity may be assayed by any method known to those of skill in the art including, but not limited to, the spectrophotometric assays that measure lysis of a gram-positive bacterial strain such as a Micrococcus strain.

As used herein, plants include both monocots and dicots, particularly crop plants and ornamental plants. Representative dicots include, but are not limited to, potatoes, tobacco, tomatoes, carrots, apples, sunflowers, petunias and violets. Representative monocots include, but are not limited to, rice, rye, corn, barley, wheat, other grasses, lilies, orchids, and palms. Preferred plants for use herein include tobacco, tomato, rice and potato.

As used herein, disease resistance refers to the ability of plants to develop fewer symptoms following exposure to a plant pathogen than a susceptible plant that does not exhibit disease resistance. Disease resistance includes complete resistance to the disease and also varying degrees of resistance manifested as decreased symptoms, longer survival or other disease parameters, such as higher yield.

As used herein, treatment includes eradication of the plant pathogen for prevention of onset and development of disease symptoms or increasing time to onset, or lessening severity of symptoms. Such decrease in disease symptoms or increase in time may be assessed by any method known to those of skill in the art to measure a parameter, such as yield, that reflects an increase in resistance or a decrease in susceptibility to a bacterial pathogen.

As used herein, heterologous or foreign nucleic acid are used interchangeably and refer to DNA or RNA that does not occur naturally as part of the genome in which it is present or which is found in a location or locations in the genome that differs from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Examples of heterologous DNA include, but are not limited to, DNA that encodes transcriptional and translational regulatory sequences and selectable or traceable marker proteins, such as a protein that confers drug resistance. Heterologous DNA may also encode DNA that mediates or encodes mediators that alter expression of endogenous DNA by affecting transcription, translation, or other regulatable biochemical processes.

As used herein, transgenic plants refer to plants in which heterologous or foreign DNA is expressed or in which the expression of a gene naturally present in the plant has been altered. Such DNA is said to be in operative linkage with plant biochemical regulatory signals and sequences. Expression may be constitutive or may be regulatable. The DNA may be integrated into a chromosome or integrated into an episomal element, such as the chloroplast, or may remain as an episomal element. In addition, any method for introduction of such DNA known to those of skill in the art may be employed.

As used herein, wild-type plant refers to plants that are of the same species or are identical to the transgenic plants, but do not contain DNA or RNA that encodes the heterologous gene that is expressed by the transgenic plant.

As used herein, mature protein, such as mature bovine lysozyme c2, refers to processed protein from which the signal and processing sequences have been cleaved.

As used herein, a precursor protein or peptide refers to a protein that includes a leader or signal sequence that effects transport of the protein through processing pathways to yield mature protein.

As used herein, a signal or leader sequence, which expressions are used interchangeably, refers to a sequence of amino acids that directs transport of the translation product through the processing pathway of the host cell and results in the generation of a mature protein. A signal sequence refers to a sequence of hydrophobic amino acids at the amino terminus of the protein to which it is linked. DNA encoding a signal sequence is located downstream (3' in the direction of transcription) from the ATG start codon and upstream (5') from the DNA that encodes the structural gene. In addition, the signal sequence includes one or a sequence of amino acids that is recognized by one or more host cell proteases. Such sequences or processing sites are interposed between the signal sequence and the protein, whereby, upon recognition of the processing site by the appropriate host cell protease, removal of the signal sequence may be effected. The signal sequence, processing sites and protein are referred to as a precursor protein, and the processed protein is referred to as the mature protein.

The signal sequences and processing sites contemplated for use herein are those that effect processing of lysozyme in transgenic plants and also in host cells, such as *P. pastoris*. Any peptide or DNA encoding such peptide that effects proper processing in plant hosts is contemplated for use herein. Preferred signal peptides and DNA encoding signal peptides are those that effect proper processing in both the selected plant host and in host cells in culture. The bovine lysozyme c signal peptide and variants thereof that effect proper processing in both transgenic plant hosts and cultured host cells constitutes the preferred signal sequence.

As used herein, operative linkage of heterologous DNA to regulatory and effector sequences of nucleotides, such as promoters, enhancers, transcriptional and translational stop sites, and other signal sequences, refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame.

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Generally, if such vectors and plasmids include origins of replication that function in the particular host cell into which the vector or plasmid is introduced, the vector, or plasmid, remains episomal. Other vectors, such as those derived from retroviruses and those derived from the Agrobacterium Ti plasmid, when introduced into an appropriate host cell, integrate into the host cell DNA. In addition, other vectors, such as the RNA virus satellite tobacco mosaic virus (STMV), remain episomal.

As used herein, expression vector includes vectors capable of expressing DNA fragments that are in operational association with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA.

Appropriate expression vectors are well known to those of skill in the art and include those that are replicable in eukaryotic cells and/or prokaryotic cells. Such expression vectors may remain episomal or may integrate into the host cell genome. Expression vectors suitable for introducing heterologous DNA into plants and into host cells in culture, such as mammalian cells and methylotrophic yeast host cells, are known to those of skill in the art. It should be noted that, because the functions of plasmids, vectors and expression vectors overlap, those of skill in the art use these terms, plasmid, vector, and expression vector, interchangeably. Those of skill in the art, however, recognize what is intended from the purpose for which the vector, plasmid or expression vector is used.

As used herein, expression cassette refers to a DNA construct that includes sequences functional for the expression, and, if desired, processing and secretion of a mature protein in a selected host. Since such fragments are designed to be moved from vector to vector and into the host cell for both replication and expression, they are often referred to by those of skill in the art as "expression cassettes". Accordingly, an expression cassette includes DNA encoding a promoter region, a transcription terminator region, and sequences sufficient for translation, as well as any other regulatory signals, such as those that effect proper processing of the expressed protein or peptide.

As used herein, the term DNA construct embraces expression cassettes and also includes DNA fragments that include more than one expression cassette.

As used herein, portions or fragments of the DNA constructs and expression cassettes are said to be operationally associated or operably linked when protein-encoding portions and regulatory regions are positioned such that expression, including transcription, translation and processing, of the protein-encoding regions is regulated by the DNA that encodes regulatory regions.

As used herein, reference to "downstream" and "upstream" refers to location with respect to the direction of transcription from the promoter which regulates transcription of the ruminant or ruminant-like pre-lysozyme c- or lysozyme c-encoding fragment.

As used herein, a DNA probe is a DNA molecule that includes a sufficient number of nucleotides to specifically hybridize to DNA or RNA that includes identical or closely related sequences of nucleotides. A probe may include any number of nucleotides and may include as few as about 10 and as many as hundreds of thousands of nucleotides. The conditions and protocols for such hybridization reactions are well known to those of skill in the art as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

As used herein, all assays and procedures, such as hybridization reactions and antibody-antigen reactions, unless otherwise specified, are conducted under conditions recognized by those of skill in the art as standard conditions.

Transgenic plants.

Transgenic plants are plants in which a heterologous or foreign gene has been inserted into the genome or into an episomal element or integrated into the genome, whereby the plant is engineered to express a desired trait, such as disease resistance or to produce a protein, which can then be isolated upon harvesting the plant.

Numerous methods for producing or developing transgenic plants are available to those of skill in the art. The method used is primarily a function of the species of plant. These methods include the use of vectors, such as the modified Ti plasmid system of *Agrobacterium tumefaciens*, the Ri plasmid system of *Agrobacterium rhizogenes* and the RNA virus vector, satellite tobacco mosaic virus (STMV). Other methods include direct transfer of DNA by processes, such as PEG-induced DNA uptake, microinjection, electroporation, and microprojectile bombardment (see, e.g., Uchimiya et al. (1989) *J. Biotech.* 12:1–20 for a review of such procedures).

Plant species, including tobacco, rice, maize, rye, soybean, *Brassica napus*, cotton, lettuce, potato and tomato, have been used to produce transgenic plants. Tobacco and other species, such as petunias, often serve as experimental models in which the methods have been developed and the genes first introduced and expressed. Generally, the DNA encoding the gene of interest is cloned or synthesized and operatively linked to regulatory regions, such as a promoter recognized by the plant RNA polymerase II, and then introduced into and expressed in tobacco. Protocols are then modified or developed for introduction into and expression of the gene in other host plants.

Examples of promoters suitable for use in plants for the expression of heterologous DNA include, but are not limited to, constitutive promoters, such as the 35S and 19S promoters of cauliflower mosaic virus (CaMV), promoters from the T-DNA genes of *Agrobacterium tumefaciens*, such as the nopaline, octopine and mannopine synthases, and developmentally or otherwise regulatable promoters.

When engineering a disease- or pathogen-resistant plant, the selected promoter should be sufficiently efficient so that at least an adequate amount of the heterologous gene product, such as lysozyme, is expressed to render the plant less susceptible to the disease caused by the plant pathogen, but not enough to cause deleterious effects in the plant. In embodiments in which the plant or seed is used as a source of the heterologous gene product, expression should be maximized, but the amount of gene product expressed should not substantially affect the yield or health of the transgenic plant in which it is expressed.

If desired, the plant promoter can be operatively linked to regulatory elements that modulate expression of the gene so that it is expressed at specific stages of development or so that the expressed protein is directed to a particular plant tissue or organ or is expressed in only a particular organ or tissue.

For example, the bovine lysozyme c signal sequence directs proper processing of mature protein in plant hosts. Thus, operatively linking DNA encoding the gene of interest to the DNA encoding this signal sequence should result in proper processing of the protein to which it is linked.
Transformation of dicots.

*Agrobacterium tumefaciens* is a ubiquitous soil bacterium which infects a wide range of dicotyledonous plants and produces crown gall tumors by introducing DNA into plant cells at wound sites. T-DNA, which causes crown galls, is integrated into the genome of the host plant. Foreign genes inserted into T-DNA through Ti plasmids, that have been modified so that they do not cause disease, are co-transferred and integrated into the host genome. In order to effect integration, only the T-DNA borders and some flanking sequences are needed in cis.
Transformation of monocots.

Since *A. tumefaciens* does not infect monocots, other methods have been developed for the introduction of heterologous DNA into monocots. Such methods include electroporation of rice, wheat and sorghum protoplasts and electroinjection through cell walls and membranes; direct and chemical-induced introduction of DNA (see, e.g., Ou-Lee et al. (1986) *Botany* 83:6815–6819; Fromm et al. (1985) *Proc. Natl. Acad. Sci. USA* 82:2037–2042; Freeman et al. (1984) *Plant Cell Phys.* 25:1353–1365; Lorz et al. (1985) *Mol. Gen. Genet.* 199:178–182; Krens et al. (1986) *Nature* 296:72–74).
Methods for introducing heterologous DNA into plants and plant cells.

DNA uptake can be accomplished by DNA alone or in the presence of polyethylene glycol (PEG-mediated gene transfer), which is a fusion agent, with plant protoplasts or by any variations of such methods known to those of skill in the art (see, e.g., U.S. Pat. No. 4,684,611 to Schilperoort et al.). Electroporation, which involves providing high-voltage electrical pulses to a solution containing a mixture of protoplasts and foreign DNA to create reversible pores in the membranes of plant protoplasts, has been used, for example, to successfully introduce foreign genes into rice and *Brassica napus*. Microinjection of DNA into plant cells, including cultured cells and cells in intact plant organs and embryoids in tissue culture has been used. Microprojectile bombardment is also used and is accomplished by accelerating small, high density particles, which contain the DNA, to high velocity with a particle gun apparatus to force the particles to penetrate plant cells and membranes.

As is evident from the Examples below, the particular protocol and means for introduction of the DNA into the plant host must be adapted or refined to suit the particular plant species or cultivar.

Upon introduction of DNA into plant host cells, the cells are cultured in vitro, generally under selective conditions. Plants are then regenerated, using methods known to those of skill in the art, from the selected cells.

Preparation of lysozyme.

Both purified lysozyme and DNA encoding a lysozyme or transgenic plants that express a heterologous lysozyme are required for practice of the methods described herein. Purified lysozyme is required for methods of treating plants, seeds and cut flowers and other plant tissues by contacting them with an effective concentration of lysozyme. DNA encoding a lysozyme is used for constructing transgenic plants that are of reduced susceptibility or are resistant to particular plant pathogens or for preparing host cells that are cultured in vitro in order to produce the lysozyme for use in treating plants, plant tissues and seeds or to replicate DNA for use in preparing transgenic plants.

Any lysozyme, and DNA encoding such lysozyme, that possesses the requisite stability and activity against gram-negative bacteria is suitable for use herein. The lysozyme may be purified from a suitable tissue or may be prepared using recombinant DNA technology. The protein may be a naturally occurring ruminant or ruminant-like lysozyme, such as bovine lysozyme c2, or may be a modified form of a ruminant or ruminant-like lysozyme, such as lysozyme encoded by DNA that has been prepared synthetically or produced by point mutation, insertion or deletion of naturally occurring, cloned or synthetic DNA. For example, bovine lysozyme c has been isolated from bovine abomasum (see, e.g., Dobson et al. (1984) *J. of Biol. Chem.* 259:11607–11616).

DNA encoding the particular lysozyme may be obtained by any method known to those of skill in the art. For example, DNA probes may be synthesized based on a partial amino acid sequence of a selected lysozyme or a lysozyme from a related species and used to screen a suitable recombinant DNA library. Alternatively, DNA may be synthesized based on a known amino acid sequence of a lysozyme. DNA constructs that include suitable promoters and other regulatory regions may be inserted into suitable vectors, plasmids or expression vectors for introduction into host cells to produce the lysozyme by culturing the host cells or for introduction into plant cells to produce transgenic plants.

DNA encoding ruminant lysozymes may be obtained by any method known to those of skill in the art. For example, DNA or RNA probes may be prepared according to a known sequence and used to screen a cDNA or genomic library to isolate DNA that encodes a protein having the known sequence or a related sequence. The DNA can then be expressed in a suitable and convenient host cell, such as a yeast host cell, and the expression product tested for stability and lytic activity by methods known to those of skill in the art or as described herein. Once it has been established that the protein product possesses the requisite stability and lytic activity, DNA constructs, including plant promoters and regulatory regions for expression of the DNA encoding the protein in a plant host cell, may be developed.

For example, ruminant lysozyme c or ruminant-like lysozyme c from sources, such as cows, bulls, sheep, goats or deer, may be prepared or obtained using methods known to those of skill in this art, including isolation of the protein using routine protein purification methods adapted to the particular species, or recombinant DNA methods, including the use of probes constructed according to amino acid sequences of the protein or according to the sequences of related DNA molecules or the sequences of related proteins, such as bovine lysozyme c2.

DNA fragments that encode a particular ruminant or ruminant-like lysozyme c may be prepared by chemical synthesis or by reverse transcription of messenger RNA (mRNA) corresponding to lysozyme-encoding DNA into complementary DNA (cDNA) followed by conversion of the cDNA into double-stranded cDNA. Genomic DNA may also be obtained by screening appropriate libraries with probes derived from the cDNA or by other methods well-known to those of skill in the art. If the lysozyme is sufficiently stable to be suitable for treating plants and plant tissues, it may be produced in cell or tissue culture or in other hosts, such as transgenic plants and animals. Alternatively, the DNA may be introduced into a plant to produce a transgenic plant that is resistant to or less susceptible to bacterial plant pathogens. Preparation of DNA constructs that encode a ruminant or ruminant-like lysozyme and expression of DNA encoding a ruminant or ruminant-like lysozyme.

The DNA construct encoding a ruminant or ruminant-like lysozyme c or pre-lysozyme c can be any DNA fragment which has a sequence that includes a translation-start-site-encoding triplet and a translation-stop-signal-encoding triplet and that encodes, starting with the translation-start triplet and ending with the triplet adjacent to the translation-stop triplet (in the 5'-direction from the stop triplet), a complete ruminant or ruminant-like pre-lysozyme c. The DNA included in the construct may be derived from mRNA or from genomic DNA. If it is derived from genomic DNA, then, for expression, it must be introduced into a host cell, such as a mammalian host cell, using a suitable vector, such as an SV40-based or retrovirus-based vector, that properly splices and processes the mRNA encoded by the genomic DNA.

DNA encoding bovine lysozyme c2 has been cloned and expressed in yeast host cells as described in abandoned U.S. application Ser. Nos. 07/265,634 and 07/115,940, which have herein been incorporated by reference (see, also Digan et al. (1989) *Bio/Technology* 7:160–164 and International Application No. WO 89/04320). The *P. pastoris* host cells, thus, serve as a means to produce bovine lysozyme for treatment of plants.

A DNA construct, including DNA encoding the lysozyme derived from a construct that was introduced into the *P. pastoris* host cells, has been engineered for introduction into plant host cells. This construct includes the approximately 460 bp EcoRI site-terminated segment that includes DNA encoding bovine pre-lysozyme c2 in operative linkage with the CaMV 35S promoter and the nopaline synthase (NOS) terminator.

Preferred DNA constructs herein contain DNA that includes a sequence of nucleotide base pairs which encodes bovine pre-lysozyme c2 (with either histidine or lysine, but preferably histidine, at position 98 of the mature protein portion) or a lysozyme that has substantially the same lytic activity and stability as bovine lysozyme c and is capable, upon transformation into a plant, of expression and proper processing, such that the resulting transgenic plant is resistant or less susceptible to a broad spectrum of plant bacterial pathogens, including both gram-negative and gram-positive pathogens. Other preferred constructs include those that are capable, upon transformation of a host, such as *P. pastoris*, of directing expression and proper processing of stable and biologically active lysozyme.

In addition, the DNA construct may include elements necessary for its selection and replication in bacteria and for its expression in suitable host cells, such as mammalian host cells, yeast host cells, and plant tissue culture host cells, to produce properly processed and biologically active lysozyme. Preferred bacterial host cells are those such as *E. coli* in which the production of large quantities of the DNA by replication can be achieved. In this regard, a plasmid which includes a segment containing the origin of replication and ampicillin-resistance or tetracycline-resistance genes of plasmid pBR322 is preferred.

Methylotrophic host cells, such as *P. pastoris*, are preferred host cells for producing large quantities of properly processed and secreted lysozyme in vitro. *P. pastoris* cells that have at least one mutation that can be complemented with a marker gene present on a transforming DNA fragment, preferably His4$^-$ (GS115) or Arg4$^-$ (GS190) auxotrophic mutant *P. pastoris* strains, are preferred host cells.

A preferred DNA construct for expression in *P. pastoris* contains the *P. pastoris* AOX1 promoter, DNA sequence encoding the bovine lysozyme precursor, and a transcription terminator derived from the *P. pastoris* AOX1 gene. Preferably, two or more such constructs are included on one DNA fragment in head-to-tail orientation.

Methods for introducing DNA into selected host cells, such as mammalian and yeast cells, or for producing transgenic plants for expression of heterologous proteins, are known in the art. Similarly, methods are known for culturing host cells, which have a gene for an heterologous protein, in order to express the heterologous protein from such a gene. Further, methods are known for isolating secreted heterologous protein from medium of such cultures.

A selectable marker gene functional in methylotrophic yeast may be employed. Such genes include those that confer an identifiable phenotype upon methylotrophic yeast cells, thereby allowing them to be identified and selectively grown from among a vast majority of untransformed cells. These known methods have been used to produce cultures of *P. pastoris* that secrete bovine lysozyme c2. Certain of these methods are described in some detail in the examples which follow.

Methods of transforming methylotrophic yeast host cells, such as *P. pastoris*, with DNA, such as vectors that contain genes for expression of heterologous proteins, are known in the art. Similarly, methods are known for culturing *P. pastoris* cells, which have a gene for an heterologous protein, in order to express the heterologous protein from such a gene. Further, methods are known for isolating from the medium of such cultures of *P. pastoris* heterologous protein that is secreted from the cells into the medium.

A preferred methylotrophic yeast host cell strain, *P. pastoris* GS115, grows efficiently on methanol in a defined minimal medium supplemented with histidine at a high-cell density and is desirable as a host system for purposes of single-cell protein production. The strain contains no bacterial replicons, antibiotic resistance genes, or other heterogeneous sequences that might be considered a potential biological hazard. Certain of these methods are described in some detail in the examples which follow.

Production of and purification of lysozyme.

In preferred embodiments, the lysozyme is prepared using a methylotrophic yeast host cell, such as *P. pastoris*, by using the promoter derived from the methanol-regulated AOX1 gene of *P. pastoris*, which is tightly regulated and can be used to promote high levels of gene expression, to regulate expression of DNA encoding the lysozyme. This gene can be the source of the transcription terminator as well.

Transformed strains, which are of the desired phenotype and genotype, are grown in fermentors. For the large-scale production of recombinant DNA-based products in methylotrophic yeast, a three-stage, high cell-density, fed-batch fermentation system is normally the preferred fermentation protocol employed. In the first, or growth stage, expression hosts are cultured in minimal medium with an excess of a non-inducing carbon source such as glycerol. When grown on such carbon sources, heterologous gene expression is completely repressed, which allows the generation of cell mass in the absence of heterologous protein expression. Next, a short period of growth under conditions of non-inducing carbon source limitation is allowed. Subsequent to the period of growth under limiting conditions, methanol alone (referred to herein as "methanol fed-batch mode"), or a limiting amount of a non-inducing carbon source plus methanol (referred to herein as "mixed-feed fed-batch mode"), are added in the fermentor, inducing the expression of the gene driven by a methanol-responsive promoter. This third stage is the so-called production stage.

The lysozyme c present in the medium of a methylotropic host cell, such as *P. pastoris*, can be readily purified by techniques well-known in the protein purification art, because of the high concentration of the enzyme and low concentration of contaminating proteins and protein fragments in the medium. A simple two-step procedure for purification is described, for example, in U.S. application Ser. No. 07/265,634, now abandoned, which has herein been incorporated by reference.

Detection and characterization of lysozyme.

Upon recovery or isolation of lysozyme from ruminant or other mammalian tissues or from host cells that express heterologous DNA encoding the lysozyme, the lysozyme is tested to ascertain whether it has the requisite stability and lytic activities.

Assays for identifying and characterizing the lytic activity of lysozyme are well-known to those of skill in the art. For example, standard spectroscopic assays measure the decrease in absorbance at a selected wavelength, such as 450 nm or 600 nm, of a suspension of a Micrococcus species, such as *M. aureus, M. luteus* and *M. lysodeiktus*.

Immunoassays and radioimmunoassays, such as those described below in Example 1, may be used to further characterize the lysozyme. The lysozyme is then tested to determine if it meets criteria for use in treating plants or for expression in transgenic plants to render them resistant to certain pathogens. The key parameters include the ability to lyse gram-negative plant pathogens, such as *Erwinia carotovora*, and stability either under field or greenhouse conditions or other conditions under which plant tissues, such as seeds, are coated or contacted with the lysozyme. The ability to lyse gram-negative plant bacteria may be tested in accordance with any method known to those of skill in the art, including kill curves and spectroscopic assays, such as those described in the Examples, below. Stability may be measured by any method known to those of skill in the art, including time courses of enzyme activity, versus time at room temperature. Preferred methods include measurements of enzyme activity following one to three hours at 30° C. or 37° C., or other measurements that reflect the ability of the lysozyme to withstand the conditions under which it is used to control or eradicate plant pathogens. Lysozyme suitable for use herein is stable following exposure to such conditions.

The selected lysozyme may then be used for treating plants, seeds, cut flowers and plant tissues as described herein, and DNA encoding the lysozyme may be introduced into plants to produce bacterial pathogen-resistant transgenic plants as described above.

Methods for treating plants by applying lysozyme to plants, seeds, cut flowers and plant tissues.

Compositions.

Sprays, powders, or other formulations that provide effective concentrations of the selected lysozyme in a suitable carrier or vehicle such as a sodium phosphate buffer, at a pH of preferably about 5–7, that are effective for reducing disease symptoms, or inhibiting the growth of the pathogen, or eradicating pathogen, are prepared. The effective concentration is preferably about 25 ppm up to about 400 ppm, and most preferably between about 125 and 250 ppm. The effective concentrations may, however, be determined empirically for the particular use and formulation of lysozyme that is prepared.

The composition may also include other agents, such as copper, that are toxic to pathogens.

Methods of treatment.

The composition may be applied by any method known to those of skill in the art. Preferred methods include spraying an effective amount of a liquid composition or a powdered composition on the plants, plant tissues, seeds or cut flowers before or after exposure to pathogen. Plant tissues and seeds can be soaked in the composition, and the lysozyme can be added to the water in which cut flowers are placed. The treatment is repeated at intervals. If the plants, plant tissues and seeds are not infected with any pathogens, they can be treated with the composition in order to render them less susceptible or resistant to the pathogens. If they are infected, then the compositions can be used to inhibit or eradicate the pathogens in order to lessen or eliminate the symptoms. The treatments may be repeated a plurality of times until the pathogen is eradicated or as long as is needed to render the plants, plant tissues and seeds less susceptible to infection. The success of the treatment may be monitored by monitoring yields or hardiness of the treated plants, plant tissues, seeds and flowers.

The particular treatment protocol may be empirically determined. For example, the plants can be treated with 10 ml, per average plant, of a composition formulated as described above for a period of at least one week and possibly daily or more until harvest.

Disinfecting seeds.

Seeds may be disinfected by contacting them with a solution or powder containing an effective concentration of the ruminant or ruminant-like lysozyme. Alternatively, the seeds may be coated with a composition that contains an effective concentration of lysozyme. Effective concentrations are concentrations that prevent, eliminate or reduce infection to permit germination and growth of plants to yield a desired crop or other harvestable product. Preferred concentrations are in the range of about 25 ppm up to about 400 ppm of the lysozyme.

An effective amount or concentration may be ascertained by any method known to those of skill in the art. For example, seeds infected with a bacterial plant pathogen, such as *Xanthomonas campestris* pv. *carotae*, which infects carrot seeds and causes carrot blight, have been soaked in solution containing either buffer, such as 0.1M sodium phosphate, pH 5.0, or in the buffer containing increasing amounts of bovine lysozyme in suspension, such as increments between 50 or 100 and 400 ppm, and then placed on shakers (250 rpm) and incubated at 37° C. Incubation has been for a time sufficient for the lysozyme to act on the bacteria, but short enough so that the incubation does not substantially affect the number of bacteria in the seeds soaked in buffer alone.

Following incubation, the seeds are spread out on absorbent paper, such as diaper paper, blotted dry and weighed to ensure that they are dry. If the seeds weigh more than prior to treatment, seeds can be incubated at 37° C. until the excess fluid evaporates. The seeds are then placed in the dark at room temperature until they are assayed for germination capability and for bacterial contamination.

Following such treatment, samples of the seeds may be tested to ascertain the effectiveness of the treatment.

Germination assays.

Germination of the treated seeds may be assayed by any method known to those of skill in the art. The seeds are assayed for germination capability to insure that the lysozyme treatment did not impair germination capability. Samples of the treated seeds are germinated, and the number of seedlings that develop from each sample can be ascertained.

Effectiveness of treatment.

The effectiveness of lysozyme treatment in reducing or eliminating bacterial infection can be assayed by any method known to those of skill in the art. For example, the seeds can be maintained under germination conditions, and the plants that are generated from the seeds are monitored for signs of infection. Effectiveness can be assessed by comparing the number of infected plants that are generated from untreated and treated infected seeds.

Alternatively, effectiveness can be assayed by plating a sample of the seeds on medium that selects for growth of particular plant pathogens (see, e.g., Schaad et al. (1988) in *A Laboratory Guide for Identification of Plant Pathogenic Bacteria*, Second Edition., Schaad, ed., APS Press).

Preparation of lysozyme from transgenic plants.

After a lysozyme has been demonstrated to be effective, DNA encoding the lysozyme may be synthesized, isolated, or otherwise cloned, and constructs suitable for the introduction into and expression of the lysozyme in plants may be prepared.

Transgenic plants, such as tomato, tobacco, rice and potato, are produced and tested to assess expression of and activity of the lysozyme produced in the plant. Any method known to those of skill in the art for assessing such expression may be used. Sample assays are set forth in the Examples.

Once expression of the lysozyme is verified, the plants may be sexually propagated by crossing with a non-transgenic plant or a transgenic plant to produce seeds that germinate into disease-resistant plants.

Alternatively, the transgenic plants, or seeds therefrom, may be planted, grown and harvested to serve as a source of the lysozyme that is expressed in the plant. The lysozyme is then isolated and purified, using standard protein purification methodology, from the harvested plants (see, e.g., Hughes et al. (1991) *Biopharm.* May 1991:18–28).

The following examples are included for illustrative purposes only and are not intended to limit the scope of the invention.

EXAMPLE 1

The procedures used to clone and express DNA encoding bovine lysozyme precursor in methylotrophic host cells are described as a model for the cloning and expression of any ruminant or ruminant-like lysozyme. Any suitable host cells, particularly eukaryotic host cells, and any methods for cloning or synthesizing DNA and expressing the DNA may be used to obtain DNA for preparing transgenic plants that express lysozyme and to produce lysozyme.

*P. pastoris* is described as a model system for the use of methylotrophic yeast hosts for heterologous protein expression. Other methylotrophic yeast host cells that can grow on methanol as a sole carbon source, from any of the four genera, Candida, Hansenula, Pichia and Torulopsis, may be used in accord with the methods described for *P. pastoris*. See, e.g., Gleeson et al. (1988) *Yeast* 4:1–15.

Expression of lysozyme in *P. pastoris*: Isolation characterization, and expression of full-length cDNA.

1. Isolation, characterization and expression of cDNA encoding bovine lysozyme c.
   a. Starting materials.

A partial bovine lysozyme c genomic clone, designated pL1, and its DNA sequence were obtained from Dr. Gino Cortopassi. Fresh bovine abomasum tissue was obtained from the Talone Meat Packing Co., Escondido, Calif., U.S.A. λgt10 and *E. coli* strain C600HFl were obtained from Clontech Labs, Inc., Palo Alto, Calif. The λgt10 packaging kit was prepared as described in Maniatis et al. (1982) *Molecular Cloning: A Laboratory Manual*, Cold Spring Harbor Laboratory Press, Cold Spring Harbor, N.Y., U.S.A. Restriction and DNA modification enzymes were obtained from Boehringer Mannheim Biochemicals, Inc. (Indianapolis, Ind.) and New England Biolabs, Inc. (Beverly, Mass.), and were used as recommended by the suppliers.

b. Preparation of bovine abomasum tissue cDNA library and isolation of a cDNA clone that encodes bovine lysozyme c2.

Total intact RNA was isolated from approximately 20 g of bovine abomasum tissue, by a modification of the method of Shields et al. (1977) *Proc. Natl. Acad. Sci. U.S.A.* 74:2059–2063. Briefly, frozen bovine abomasum tissue was powdered in a stainless steel manual pulverizer in the presence of liquid nitrogen. The powdered tissue was added to 100 ml of proteinase K buffer (0.14M NaCl, 0.05M Tris pH 7.4, 0.01M EDTA pH 8.0, 1% sodium dodecyl sulfate (SDS)) containing 400 μg/ml proteinase K (Boehringer Mannheim Biochemicals, Inc., Indianapolis, Ind.). The mixture was immediately shaken well and then incubated at room temperature for 15 minutes. After incubation, the preparation was extracted with an equal volume of PCIA (phenol:chloroform:isoamylalcohol, 25:24:1) followed by extraction with an equal volume of CIA (chloroform:isoamylalcohol, 24:1). The resulting DNA/RNA mixture was precipitated by adjusting the NaCl concentration to 0.25M, adding 2 volumes of ethanol, and placing the solution at −20° C. overnight. After centrifugation at 5000×g for 60 minutes, the DNA/RNA was resuspended in 20 ml of ETS buffer (0.1M Tris, pH 7.6, 0.01M EDTA, 0.2% SDS). PCIA and CIA extractions, and DNA/RNA precipitations were performed as described above. The DNA/RNA precipitate was collected by centrifugation and was resuspended in 32 ml of 10 mM Tris, 10 mM EDTA, pH 7.4. Following resuspension, the RNA present in this solution was layered onto CsCl (1 g CsCl/ml) in 4 tubes and centrifuged (Beckman SW41 rotor) at 37,000×g for 20 hours. The RNA pellets were resuspended in 8 ml of ETS buffer, ethanol precipitated twice (by addition of NaCl to a final concentration of 0.25M NaCl and then adding two volumes of 95% ethanol), and resuspended in 5 ml of ETS buffer. Polyadenylated (poly(A)$^+$) RNA was selected from the solution by affinity chromatography on oligodeoxythymidylate (oligo-dT) cellulose columns (Aviv et al. (1972) *Proc. Natl. Acad. Sci. U.S.A.* 69:1408–1412).

Ten μg of the polyadenylated RNA was denatured in 2 mM CH$_3$HgOH (Alpha Products, Danver, Mass.) for 5 minutes at room temperature. Following the protocol of Huynh et al. ((1984) pp. 49–78 in *DNA Cloning: A Practical Approach* (D. Glover, ed.), IRL Press, Oxford), a cDNA library in λgt10 (Gubler et al. (1983) *Gene* 25:263–269; Lapeyer et al. (1985) *Gene* 37:215–220) was generated from total poly(A)$^+$ mRNA.

Briefly, cDNA was prepared by reverse transcribing the mRNA with mouse Moloney leukemia virus (MMLV) reverse transcriptase. This was followed by RNase H treatment and DNA polymerase I-mediated second cDNA strand synthesis to generate double-stranded cDNA. Following second-strand synthesis, the cDNA was made blunt-ended with S1 nuclease. To insure that the ends were completely blunt-ended, the ends were treated with *E. coli* DNA polymerase I Klenow fragment (Telford et al. (1979) *Proc. Natl. Acad. Sci. USA* 76:2590–2594). EcoRI adaptors (Wood et al. (1984) *Nature* 312:330–337) were ligated to the double-stranded cDNA. Excess adaptors were removed by chromatography over a Sepharose CL-4B column equilibrated with 10 mM Tris, pH 7.4, 1 mM EDTA, and the column fractions containing cDNAs larger than 400 bp in size were pooled and ligated into cDNA bacteriophage cloning vector λgt10, which had been EcoRI-digested and phosphatase-treated. Ligations were performed in a 5 μl volume and incubated at 16° C. for 18 hours. The reaction contained 1 μg of λgt10 vector (final concentration=200 μg/ml) and 50–100 ng of cDNA (2- to 4-fold molar excess of insert over vector). The cDNA was packaged, using a λ packaging kit, and the resulting vectors were plated on *E. coli* strain C600HFl, and plaques were screened with radiolabelled pL1. Those plaques which were identified as containing cDNA coding at least part of bovine lysozyme c were plaque-purified (Maniatis et al. (1982) *Molecular Cloning: A Laboratory Manual*, Cold Spring Harbor Laboratory Press, Cold Spring Harbor, N.Y., USA) and screened with both pL1 and an oligonucleotide probe that encompassed DNA sequences encoding amino acids 29–38 of mature bovine lysozyme c2.

Plaque lifts were performed essentially as described by Benton et al. (1977) *Science* 196:180–182. Nitrocellulose filters were prehybridized for 4 hours at 42° C. in 5× SSPE (0.9M NaCl, 0.04M NaOH, 0.05M $NaH_2PO_4$-$H_2O$, 0.005M EDTA, pH 7.0), 5× Denhardt's solution, 50% (v/v) formamide, 0.2% (w/v) SDS and 200 μg/ml sheared herring sperm DNA (Boehringer Mannheim Biochemicals, Inc., Indianapolis, Ind.). The 50× Denhardt's stock solution contains 5 g Ficoll 400 (Pharmacia, Inc., Piscataway, N.J., catalog No. 17-0400-01, average molecular weight approximately 400,000 daltons), 5 g polyvinylpyrrolidone PVP-360 (Sigma Chemical Co., St. Louis, Mo., average molecular weight approximately 360,000 daltons), 5 g bovine serum albumin in $H_2O$ to bring volume to 500 ml. After the nick-translated probe pL1 was added directly to the prehybridization solution at 1×10⁶ cpm/ml, the filters were hybridized for 16 hours at 42° C. and then washed several times, for 15 minutes per wash, in 0.1× SSPE, 0.1% (w/v) SDS at 65° C., and autoradiographed. For oligonucleotide screening, the filters were prehybridized in 6× SSPE, 5× Denhardt's solution, 25% formamide, 0.2% (w/v) SDS and 200 μg/ml herring sperm DNA for 2 hours at 42° C. They were then hybridized for 3 hours in the same buffer at 42° C. and washed several times in 1× SSPE at 45° C.

One of the plaque-purified clones, which hybridized to the oligonucleotide, was designated BL3. BL3 included a 950 bp cDNA insert. The sequence of the cDNA insert of clone BL3, which is set forth in Sequence ID No. 1, includes EcoRI adaptors at the 5' and 3' termini, a 436 bp region that encodes bovine lysozyme c2, and a 482 bp 3'-untranslated noncoding sequence. The 3'-noncoding sequence in BL3 does not contain a polyadenylation signal or a poly(A)⁺ tail. DNA sequencing at the 5'-terminus of the cDNA insert in BL3 indicated that the insert contains 49 bp encoding the C-terminal portion of the protein signal sequence, but does not contain the ATG triplet corresponding to the translation initiation codon of the pre-lysozyme c2 mRNA. The insert in BL3 was identified as DNA encoding a bovine lysozyme c2, the most abundant of the three bovine lysozyme c proteins. The only difference between the protein encoded by this DNA and the sequence for bovine lysozyme c2 reported by Jolles et al. ((1984) *J. Biol. Chem.* 259:11617–11625) is a lysine to histidine change at position 98 of the mature protein. The presence of the histidine residue at this position was confirmed by N-terminal analysis of the C-terminal CNBr fragment of the protein expressed from the insert. Furthermore, sequencing of lysozyme c2 from bovine abomasum tissue indicated that the amino acid at position 98 is histidine. Subsequent sequencing of the bovine lysozyme mRNA indicated that the BL3 insert lacks 5 bp of coding sequence at the 5'-end, including the initiation ATG codon. Such sequencing indicated that the first amino acid following the initiating methionine was lysine.

The DNA encoding bovine lysozyme c that was subsequently used for preparing transgenic plants was the insert, for which the sequence is set forth in Seq. ID No. 1, from BL3, but modified as described above, to include DNA encoding Met and Lys immediately before the Ala, so that the resulting DNA encodes the entire bovine lysozyme precursor. The DNA was also further modified by removal of the 3' untranslated sequence.

c. Construction of expression vectors.

Two in vitro M13 mutagenesis procedures were performed, one on each of the 5'- and 3'-ends of the bovine pre-lysozyme c2 coding region of BL3, prior to insertion of the coding region into the *P. pastoris* expression vector pAO804 (see, International Application No. WO 89/04320; see also, U.S. application Ser. No. 07/265,634, to Digan et al. now abandoned) in order to modify the coding region to make the region compatible with the expression vector and to make some other desired changes. The 3'-end of the coding region was mutagenized to remove the 482 bp of noncoding sequence and to introduce an AsuII restriction enzyme site (5'-TTCGAA-3'), and an EcoRI restriction enzyme site (5'-GAATTC-3'), immediately 3' to the TAA triplet encoding the translational stop codon. The 5'-end of the insert, in a clone (designated pBL4C) identified as having these changes at the 3'-end, was mutagenized to introduce a seven-base-pair sequence (5'-ATGAAGG-3'). This modification at the 5'-end completed the coding sequence for the N-terminus of the signal sequence (Met-Lys-Ala . . . ) and added a second EcoRI restriction site directly before the Met codon-encoding ATG. Clone pBL16C was identified as possessing both of the desired mutagenized ends.

The bovine pre-lysozyme c2 coding fragment bounded by EcoRI sites from pBL16C was inserted into the unique EcoRI site of pAO804 in such a manner that the lysozyme sequence is oriented operatively for transcription from the AOX1 promoter. When *P. pastoris* cells transformed with the plasmid (or the BglII-site-terminated expression unit thereof) were grown with methanol as a carbon source, pre-lysozyme c2 was expressed under transcriptional control of the AOX1 promoter.

Double-stranded DNA from the replicative form of pBL16C was cut with EcoRI, and the resulting, approximately 460 bp, EcoRI fragment was ligated into EcoRI-cut and alkaline phosphatase-treated pAO804 DNA (Alkaline phosphatase was obtained from Boehringer Mannheim Biochemicals, Inc., Indianapolis, Ind.). One of the two resulting expression plasmids, which was designated pSL12A, has the correct 5' to 3' orientation of the bovine lysozyme coding sequence relative to the position and orientation of the AOX1 promoter and transcription start site in the "5'-AOX1" promoter segment and the "3'-AOX1" terminator segment.

d. Expression of bovine lysozyme c2 using GS115 cells.

Plasmid pSL12A was digested with SalI, and the resulting fragment, which encodes bovine lysozyme c2 and which has termini that include sequences homologous to regions 5' and 3' of the *P. pastoris* HIS4 gene, was introduced into *P. pastoris* GS115, using a whole-cell lithium chloride yeast transformation system.

*P. pastoris* strain GS115 ((His4$^-$) (see, Cregg et al. (1985) *Mol. Cell. Biol.* 5:3376–3385), a histidine-requiring auxotroph of *P. pastoris*, which was previously determined to be defective in histidinol-dehydrogenase (HIS4) and to possess a reversion frequency to histidine prototrophy of less than $10^{-8}$, was used as the gene expression host for transformation with pSL12A. *P. pastoris* GS115 grows efficiently on methanol in a defined minimal medium supplemented with histidine at a high-cell density and is desirable as a host system for purposes of single-cell protein production.

A whole-cell lithium chloride yeast transformation system, modified from that described for *Saccharomyces cerevisiae* (Ito et al. (1984) *Agric. Biol. Chem.* 48:341–347), was used to introduce the linear DNA fragments into GS115. A 50 ml shake-flask culture of *P. pastoris* strain GS115 was grown in YPD (10 g Bacto-yeast extract, 20 g Bacto-peptone, 20 g dextrose, 20 g Bacto-agar, 1000 ml distilled water) at 30° C. with shaking to an $OD_{600}$ of approximately 1.0 ($5 \times 10^7$ cells/ml). The density at harvest can be from 0.1 to 2.0 $OD_{600}$ Units. After the cells were washed once in 10 ml of sterile $H_2O$, and after pelleting by centrifugation at approximately 1500×g for 3–5 minutes, they were pelleted again by the same procedure and then washed once in 10 ml of sterile TE buffer (10 mM Tris-HCl, pH 7.4, 1 mM EDTA). The cells were resuspended in 20 ml of sterile lithium chloride plus TE buffer (0.1M LiCl, 10 mM Tris-HCl, pH 7.4, 1 mM EDTA) and incubated at 30° C., with occasional shaking, for one hour.

A sterile 12×75 mm polypropylene tube, containing 10 μg of HaeIII-digested *E. coli* carrier DNA, 2 μg of the SalI-digested DNA from plasmid pSL12A and 0.1 ml of competent *P. pastoris* cells in lithium chloride plus TE buffer with was incubated in a water bath at 30° C. for 30 minutes. Approximately 0.1–20 μg of vector DNA can be used to transform the cells. 0.7 ml of 40% polyethylene glycol ($PEG_{3350}$, Fisher Scientific, Fair Lawn, N.J.) in lithium chloride plus TE buffer was added, and the tube was vortexed briefly and again incubated in a water bath for 30 minutes at 30° C. After the cells were heat shocked for 5 minutes at 37° C., the mixture was centrifuged and then resuspended in 0.1 ml sterile $H_2O$. The cells were then spread on selective plates (0.67% Yeast Nitrogen Base, without amino acids, 2% glucose, 2% agar) and then incubated for three days at 30° C.

Cells from selected colonies were grown in shake flasks for 4–5 days in 100 mM sodium phosphate-buffered minimal media containing 0.2% glycerol and 1% methanol to a density of between 4 and 5 $OD_{600}$ units/ml. The final level of bovine lysozyme c2 accumulated from the cells in the media was 0.24 and 0.42 mg/L.

2. Assays for identifying and assessing the biological activity of lysozyme.

a. Immunoassays for bovine lysozyme.

Bovine lysozyme c2 for use as a standard and for preparing antisera was purified according to the procedure described by Dobson et al. ((1984) *J. of Biol. Chem.* 259:11607–11616). As reported by Dobson et al., three distinct peaks corresponding to bovine stomach lysozymes c1, c2 and c3, were evident by absorbance (A) at 280 nm after column chromatography on Whatman CM52. Each of the three bovine stomach lysozyme peaks contained lysozyme activity, as measured in a spectrophotometric assay, described below, and approximately 2 mg of protein. Purity of the bovine lysozyme c2 protein was estimated at greater than 95% after polyacrylamide gel electrophoresis on a 15% polyacrylamide gel.

All of the assay results are dependent upon quantitation with an aliquot of the purified bovine lysozyme dialyzed against 1× PBS and stored at −20° C. For the results described below, the standard has been quantified using the published extinction coefficient for a 1% solution measured at $280_{nm}$, $\epsilon=28.2$ (Jolles et al. (1984) *Mol. Cell. Biochem.* 63:165–189).

Antisera raised in rabbits against bovine lysozyme c2 was prepared by standard protocols. Briefly, two young, male, white, New Zealand rabbits were each immunized with 250 μg of bovine lysozyme c2, purified as described above and dialyzed against 1× PBS before the injections. The rabbits were each boosted with 100 μg of lysozyme c2 30 days later and boosted again ten days later with another 100 μg of protein. While the initial immunizations were performed with lysozyme c2 emulsified with Freund's complete adjuvant (Difco Labs, Detroit, Mich.), Freund's incomplete adjuvant (Difco Labs, Detroit, Mich.) was used for the boosts. The rabbits were bled for antisera one week after the last boost.

Antisera from both rabbits were tested by placing different amounts of native and denatured purified bovine lysozyme c2 and bovine serum albumin (Sigma Chemical Co., St. Louis, Mo.) in phosphate-buffered saline, binding to nitrocellulose filters that had been incubated with different dilutions of the antisera, using a "slot blot" apparatus (Schleicher and Schuell, Inc., Keene, N.H.), and using a standard immunoblot protocol (Towbin et al. (1979) *Proc. Natl. Acad. Sci. U.S.A.* 76:4350–4354). The buffer used for filter blocking and washing, and the antibody and $^{125}$I-protein A dilution, was composed of 1× PBS (140 mM sodium chloride, 3 mM potassium chloride, 10 mM disodium phosphate, 2 mM monopotassium phosphate, pH 7.2), 0.25% gelatin (Bio-Rad, Inc., Richmond, Calif.), 0.05% Tween-20 (Sigma Chemical Co., St. Louis, Mo.) and 0.02% sodium azide (Sigma Chemical Co., St. Louis, Mo.). The sera from one rabbit, designated #156, was chosen due to the substantially lower cross-reactivity of this sera with bovine serum albumin. Using a 1:2500 dilution of the sera from rabbit #156, 2.5 ng of the lysozyme standard was easily detectable on a slot blot, and 25 ng gave a very strong signal.

b. Bioassays for secreted bovine lysozyme.

*Micrococcus luteus* and *Micrococcus lysodeiktus* cells were obtained from Sigma Chemical Company, St. Louis, Mo.

Spectrophotometric and halo assays, which measure the ability of lysozyme to lyse *M. luteus*, were used to analyze the bioactivity of the secreted bovine lysozyme c2, as described in Grosswicz et al. ((1983) *Meth. Biochem. Analys.* 29:435), but conducted at pH 5.0 rather than pH 7.0 as prescribed for egg white lysozyme. The halo assay is an in vitro assay which results in a halo of lysis of *M. luteus* cells on agar plates. Using the halo assay, 10 μl samples were added to 2 mm holes punched in an agarose plate composed of 1% agarose and 1.2 mg/ml dried *M. luteus* cells in 0.1M phosphate buffer, pH 5.0. The diameters of the resulting halos were measured after a 16-hour incubation at room temperature and quantified by comparison to a semilog plot of halo diameter versus amount derived by using the lysozyme standard. The plot was linear from 100 ng to 10

μg. The lower limit of sensitivity of the assay is approximately 50 ng and, using this assay, the minimum detectable concentration was 5 mg/L of purified bovine lysozyme c2.

The spectrophotometric assay measured in vitro lysis of dried *M. luteus* cells. Samples of varying amounts of lysozyme were added to a 0.3 mg/ml suspension of dried cells in 0.1M phosphate buffer, pH 5.0. Cell lysis was monitored by recording the decrease in absorbency at 450 nm every 15 seconds over a 2 minute period. The slope of the line was calculated by linear regression and quantitated by comparing this slope to a line on which slopes versus concentration of the purified standard were plotted. The minimum detectable concentration of the spectrophotometric assay was 5 mg/L.

c. Radioimmunoassays (RIAs).

Radioimmunoassays (RIA) have been used in order to evaluate the activity of the lysozyme. Radioiodination of lysozyme, for use as tracer in RIAs, was carried out using the IODOBEAD™ method. Briefly, one iodobead (Pierce Chemical Co., Rockville, Ill.) was added to a reaction mixture containing 1 mCi Na$^{125}$I (New England Nuclear, Boston, Mass.), 50 μg purified lysozyme c2 in 50 μl, and 10 μl of 0.5M sodium phosphate buffer, pH 7.3, and incubated for 30 minutes on ice. Subsequently, the contents of the reaction vial were transferred to a prepacked G-25 desalting column (PD-10 from Pharmacia, Piscataway, N.J.) and eluted with 50 ml of 0.05M sodium phosphate buffer, pH 7.3, containing 0.05% crystalline bovine serum albumin. The fractions were counted in a Micromedic Gamma Counter, and the position of $^{125}$I-lysozyme was determined. The iodinated preparation was tested by precipitation in 10l trichloroacetic acid (TCA) to estimate the proportion of intact peptide. Typically, $^{125}$I-lysozyme preparations used in RIAs were greater than 98% TCA-precipitable.

The RIAs, by which the concentration of bovine lysozyme c2 in *P. pastoris* culture samples was determined, were carried out in a standard protocol involving incubation of varying amounts of standard or unknown samples with 1:25000 final dilution of rabbit anti-lysozyme antibody, 10,000–20,000 counts of $^{125}$I-lysozyme in a final volume of 500 μl of assay buffer (50 mM sodium phosphate, 0.1M NaCl, 25 mM EDTA, 0.1% sodium azide, 0.1% bovine serum albumin (Fraction V), 0.1% Triton X-100, pH 7.4). Subsequent to incubation overnight at 4° C., 100 μl of 1:40 dilution of Pansorbin® (Calbiochem, San Diego, Calif.) suspension of *S. aureus* cells coated with Protein A was added and incubated for 15 minutes at room temperature. The tubes were centrifuged for 60 minutes at 2360×g after addition of 2 ml of ice-cold wash buffer (0.9% NaCl, 5 mM EDTA, and 0.1% Triton X-100). The supernatant was decanted, and the pellets were counted for $^{125}$I-lysozyme. Under these conditions, approximately 50% of total $^{125}$I-lysozyme was recovered in the pellet in the reference tube and 10% in the nonspecific binding tube, i.e., in the presence of excess unlabeled lysozyme. The sensitivity range for the assay was 0.2–20 ng with an ED$_{50}$ of approximately 2 ng. The unknown samples were assayed at three dilutions each, in duplicate. Total binding in the absence of unlabeled lysozyme was measured, and the ED$_{50}$ for the competition of the $^{125}$I-lysozyme by unlabeled lysozyme determined.

d. Miscellaneous materials and methods.

SDS-PAGE analyses were performed essentially as described by Laemmli ((1970) *Nature* 227:680–685). Each sample was diluted 1:1 in 2× sample buffer (0.125M Tris HCl, pH 6.8, 4% SDS, 200 mM DTT, 20% glycerol, 0.005% bromophenol blue, 20 μg/ml pyronin Y) and boiled for 10 minutes before separation in a Mini-Protean gel apparatus (BioRad, Richmond, Calif.) on either a 15% acrylamide gel with a 5% stacking gel or a 17–27% gradient Sepragel precast gel (Integrated Separation Systems, Hyde Park, Mass.). Protein standards (BioRad, Richmond, Calif.) were included as molecular weight markers.

Alternatively, SDS-PAGE analyses were performed in a tricine system as described by Schagger and von Jagow ((1987) *Anal. Biochem.* 166:368–379) on a 16% acrylamide gel with a 4% stacking gel. The 2× sample buffer for the tricine system contained 8% SDS, 24% glycerol, 0.1M Tris-HCl, pH 6.8, 200 mM DTT, 0.004% Coomassie Brilliant Blue G.

Gels were stained with Coomassie Brilliant Blue R followed by silver. For Coomassie staining, gels were stained overnight in 50% ethanol, 10% acetic acid, 5% TCA, 200 mg/L Coomassie Brilliant Blue. The following day the gels were rehydrated for one hour in 10% ethanol, 10% acetic acid, 1% TCA, 50 mg/L Coomassie Brilliant Blue, and then destained in 10% ethanol, 10% acetic acid. Silver staining was accomplished essentially as described by Morrissey ((1981) *Anal. Biochem.* 117:304–310) without the glutaraldehyde fixation.

Cell extracts and cell-free broth samples analyzed by immunoblot were first separated by SDS-PAGE, as described above. The gels were not subjected to staining. Transfer of protein to a 0.45μ nitrocellulose membrane was carried out for 1.5 hours at 0.1 amps. The membrane was blocked with Western buffer (0.25% gelatin, 1× PBS, 0.05% Tween-20, 0.02% sodium azide) at 37° C. for 1 hour before incubation overnight at room temperature in Western buffer containing a 1:2,000 dilution of polyclonal antisera to lysozyme isolated from bovine urine. The membrane was then washed extensively (four 15-minute washes) with Western buffer, incubated with approximately 3 μCi $^{125}$I-Protein A (New England Nuclear, Boston, Mass.) at room temperature for 60 minutes, washed extensively as before, air dried, and exposed to film. Under these conditions, as little as 1 ng of bovine lysozyme can be detected.

EXAMPLE 2

Bovine lysozyme is highly stable at room temperature.

Activity of the recombinant bovine lysozyme was assessed using the standard spectrophotometric assay in which the amount of lysozyme-induced lysis of *M. lysodeikticus* cell walls was measured. Protein concentrations for samples were determined by the Lowry method, with and without TCA precipitation. A solution of 3 mg/ml *M. lysodeikticus* in 0.1M NaPO$_4$, pH 5 was used. This substrate solution was freshly prepared, using frozen cells, which were diluted 1:1 with the phosphate buffer to form a cell suspension. A stock solution of recombinant lysozyme was prepared by dissolving about 2 mg of lyophilized *P. pastoris*-produced (see Example 1) recombinant bovine lysozyme, which had been stored at room temperature for 5 days, following storage at −20° C., in 1 ml of 0.1M NaPO$_4$, pH 5 buffer. A similar stock solution of the standard, purified bovine stomach lysozyme, which had been stored at −20° C., was also prepared. For each assay, lysozyme stock solution was diluted 1:100 in 0.1M NaPO$_4$ buffer, pH 5. Ten μl of the diluted enzyme was added to 990 μl of the *M. lysodeikticus* suspension, and the decrease in absorbance (A) at 450 nm was measured using a Beckman DU-8 with kinetics package. A unit of activity was defined as a 1% absorbance change per minute at 450 nm, 25° C., at pH 5. The starting absorbance of the cell suspension was used as the reference against which the absorbance change was measured.

The data indicated day-to-day variability, which is probably attributable to instrument error and which was not correlated with differences in lysozyme treatments, storage or source. As indicated in the Table, the recombinant bovine lysozyme and the stomach lysozyme exhibited a similar level of stability.

TABLE 1

STABILITY OF BOVINE LYSOZYME

| Run No. | Recombinant lysozyme | Stomach lysozyme |
|---|---|---|
| #1 Concentrated[A] unlyophilized | 8.65 U/μg | 11.5 U/μg |
| #2 Lyophilized sample brought up in H$_2$O | 4.07 U/μg<br>4.09 U/μg | 3.3 U/μg<br>2.8 U/μg |
| #3 Lyophilized sample brought up in 0.1M NaPO$_4$, pH 5 | 5.98 U/μg<br>5.60 U/μg | 5.5 U/μg<br>4.5 U/μg |
| #4 Lyophilized sample left at room temperature for 5 days brought up in 0.1M NaPO$_4$, pH 5 | 7.53 U/μg<br>5.57 U/μg | 4.56 U/μg<br>4.59 U/μg |

[A]Concentrated *P. pastoris*-produced lysozyme was obtained by concentrating the cell-free fermentation broth, of a recombinant bovine lysozyme secreting *P. pastoris* strain, through filtration using a 3000 MW cut-off spiral cartridge filter.

EXAMPLE 3

Bovine lysozyme inhibits plant pathogens in vitro.

The effectiveness of chicken, bovine and human lysozyme in inhibiting the growth of plant bacterial pathogens in vitro was tested. The tests included the gram-negative bacterial strains *Agrobacterium tumefaciens* strain C58, *Pseudomonas syringae* pv. *tomato, Xanthomonas campestris* pv. *malvacearum* and *Erwinia carotovora* subsp. *carotovora*, and the gram-positive bacterial strain *Clavibacter michiganensis*.

A. Procedure.

Prior to use, each lysozyme was tested in the *M. lysodeikticus* assay discussed above. In this assay, lysozyme activity was defined as the rate of decrease in absorbance at 600 nm of a sample of *M. lysodeikticus* at 25° C. per minute per mg of lysozyme at pH 5.0. The rates of decrease in absorbance in the presence of chicken, human and bovine lysozyme were 9.1, 8.7, and 6.6 O.D. (optical density)/min/mg, respectively, which confirmed that each lysozyme sample was biologically active.

Approximately 1×10$^6$ bacteria of each species were inoculated into 3 ml of Luria broth, containing 0, 25 or 50 ppm of *P. pastoris*-produced bovine lysozyme, *P. pastoris*-produced human lysozyme, or hen egg white lysozyme (Sigma, St. Louis, Mo.). The pH of the nutrient broth was adjusted to 5.5 for bovine and chicken lysozyme and to 7.5 for human lysozyme. The cultures were incubated overnight at 30° C. on a rotary shaker at 300 rpm. The O.D. at 600 nm was measured after 24 hours of growth of *A. tumefaciens, X. campestris* pv. *malvacearum* and *E. carotovora* subsp. *carotovora* in the presence of each of the lysozymes, after 48 hours of growth of *P. syringae* pv. *tomato* in the presence of each of the lysozymes, and *C. michiganensis* in the presence of human lysozyme, and after 72 hours of growth of *C. michiganensis* in the presence of bovine or chicken lysozyme.

Each assay was repeated 5 times.

B. Results.

To normalize the data, the O.D. of cultures incubated in the presence of each lysozyme was compared to controls that were incubated in the absence of each lysozyme. The data were reported as the percentage of the control O.D.

The results indicated that bovine lysozyme was effective in inhibiting the growth of gram-negative bacteria. This is significant since the majority of plant pathogens are gram-negative bacteria. In most assays, bacterial growth was inhibited nearly 50% in the presence of only 25 ppm of bovine lysozyme. Chicken and human lysozyme were ineffective in inhibiting the growth of gram-negative bacteria. All three lysozymes were effective in inhibiting the growth of gram-positive bacteria. Substantially greater than 50% inhibition was achieved at concentrations of each lysozyme of 25 ppm.

EXAMPLE 4

Preparation of transgenic tobacco, tomato, potato and rice plants transformed with DNA that encodes bovine lysozyme precursor.

A. Preparation of *A. tumefaciens* that carries the pBIN19::35S/BVLZ/NOST plasmid.

Plasmid pBL816 contains the entire coding sequence of the pre-bovine lysozyme c2 (BVLZ) gene. The coding region includes DNA as set forth in Seq. ID No. 1, except that it also includes the nucleotides ATGAAG (Met Lys) inserted immediately upstream of the nucleotides that encode Ala Lys Val, so that the entire native bovine lysozyme signal peptide is encoded in the plasmid. Plasmid pBL816 was digested with EcoRI, and the approximately 433 bp EcoRI fragment that contains the coding region was purified by agarose gel electrophoresis and made blunt-ended by treatment with T4 DNA polymerase.

Plasmid pSL12A, described above, is pAO804 with the EcoRI fragment from pBL16C. Plasmid pBL816 is pAO815 with the same fragment inserted therein. For a description of the construction of pAO815, see, International Patent Application WO90/10697 which is based on U.S. patent application Ser. No. 323,964 to Siegel et al., now U.S. Pat. No. 5,102,789.

Plasmid pBI121, an Agrobacterium Ti plasmid-based plant transformation vector, was purchased from Clontech (Palo Alto, Calif.). Plasmid pBI121 contains the *E. coli* β-glucuronidase (GUS) gene under the control of the cauliflower mosaic virus (CaMV) 35S promoter, the nopaline synthase (NOS) terminator, and the gene for kanamycin resistance.

The GUS gene was excised from pBI121 as an XbaI-SstI fragment, and the remaining vector fragment was retained and made blunt-ended by treatment with T4 DNA polymerase following purification by agarose gel electrophoresis. The blunt-ended vector fragment was ligated to the blunt-ended BVLZ gene from pBL816, and the resulting construct was introduced into *E. coli* DH5α cells and cultured. Kanamycin-resistant colonies were picked and screened for plasmids that contained the BVLZ gene oriented in a sense direction with respect to the CaMV 35S promoter and the NOS transcription terminator. The selected plasmid was named pBIN19::35S/BVLZ/NOST.

The plasmid, pBIN19::35S/BVLZ/NOST, in *E. coli* DH5α cells, was mobilized via triparental mating into *A. tumefaciens* strain LBA4404 (Clontech, Palo Alto, Calif.) using the helper plasmid pRK2073, a gift from Dr. Gary Ditta, U.C.S.D, contained in *E. coli* HB101. *A. tumefaciens* colonies carrying the pBIN19::35S/BVLZ/NOST plasmid were selected by plating the mixture of the three bacteria on M9 sucrose media, which contained kanamycin. Since both *E. coli* strains were auxotrophs, only the *A. tumefaciens* bacteria that contain pBIN19::35S/BVLZ/NOST could grow on this medium. Single colonies were selected.

B. Preparation of transgenic tobacco plants that express bovine lysozyme.

Single colonies of the *A. tumefaciens* bacteria that contained pBIN19::35S/BVLZ/NOST were selected and used to transform tobacco by co-cultivation with leaf discs (Horsch et al. (1988) "Leaf disc transformation", *Plant Molecular Biology Manual*, Gelvin, S. B., Schilperoort, A., and Verma, D. P. S., eds., pp. A5/1–9). Approximately 500 kanamycin-resistant tobacco plants were obtained, and 100 of these have been maintained in tissue culture.

Eleven of the 100 kanamycin-resistant tobacco plants in culture were randomly selected and tested for the production of bovine lysozyme by immunoblot analysis. Extracts were prepared by grinding the tissue (100 mg) in liquid nitrogen and adding 250 µl 0.25M Tris phosphate, pH 6.7, containing 1 mM dithiothreitol and 1 mM EDTA. This mixture was vortexed, centrifuged at 12,000×g at room temperature, and the supernatant was retained. Samples were adjusted by dilution with water to contain equal amounts of total protein per µl, and 1 µg of protein of each sample was loaded per lane of a 10% polyacrylamide gel containing 0.1% SDS (Laemmli (1970) *Nature* 227:680–685). An extract from a non-transformed plant and 50 ng of purified *P. pastoris*-produced bovine lysozyme were included as controls.

The samples were heated for 4 minutes in SDS-containing loading buffer at 95° C., prior to loading the samples on the gel. Following electrophoresis, the proteins were electrotransferred to a nitrocellulose membrane, and the membrane was exposed to polyclonal rabbit antisera raised against bovine lysozyme and reacted with goat anti-rabbit IgG antisera conjugated to alkaline phosphatase. The proteins that reacted with the antibodies were detected using the Western Blot Alkaline Phosphatase system of Promega (Madison, Wis.). Each of the transgenic plants expressed varying amounts of the *P. pastoris*-produced bovine lysozyme.

Comparison of the size of the bovine lysozyme protein expressed in the plants with that expressed in *P. pastoris* indicated that the signal sequence was correctly cleaved in the transgenic tobacco plants.

C. Preparation of transgenic tomato plants.

Transgenic tomato plants (*Lycopersicon esculentum* cv. UC82) transformed with pBIN19::35S/BVLZ/NOST have also been produced.

The transformation of seedlings of *L. esculentum* cv. UC82 (Ferry-Morse Seed Co., Modesto, Calif.) was performed substantially according to the protocol of Fillatti et al. (1987), *Bio/Technology* 5:726–730, with modifications as described below.

Cotyledons were excised from eight-day-old tomato seedlings germinated in vitro and were cut into three sections. The middle sections with dimensions 0.5 cm×0.25 cm were placed abaxile side up on one-day-preconditioned tobacco feeder plates containing KCMS incubation medium (Mirashige and Skoog salt base with thiamine-HCl, 1.3 mg/l; 2,4-α-dicholorphenoxyacetic acid, 0.2 mg/l; kinetin, 0.1 mg/l; potassium phosphate monobasic, 200 mg/l; myo-inositol, 100.0 mg/l; sucrose, 30.0 mg/l; tissue culture agar 8.0 g/l, pH 5.7) and incubated at 27° C. with 16 hours of light per day.

The tobacco feeder plates were prepared according to the method of Horsch and Jones (1980) *In Vitro* 16:103–108, with the following modifications. Cells from a six-day-old suspension culture were resuspended in fresh MM medium (Murashige and Skoog salt base with thiamine-HCl, 0.1 mg/l; pyridoxine-HCl 0.5 mg/l; nicotinic acid, 0.5 mg/l; glycine 2.0 mg/l; 6-benzlyaminopurine, 0.5 mg/l; 2,4-α-dichloro-phenoxyacetic acid, 0.5 mg/l; myo-inositol, 100.0 mg/l; sucrose 30.0 g/l, pH 5.7) to a final density of 0.3 g fresh weight per ml.

The suspension was stirred, and 1.5 ml aliquots were pipetted onto KCMS medium (25 ml) solidified with tissue culture agar (0.8% W/V) in 100 mm×20 mm plastic petri plates. After one day of incubation, the explants were floated in 20 ml of Murashige and Skoog liquid medium without hormones containing an overnight culture of *A. tumefaciens* strain LBA4404 (Clontech, Palo Alto, Calif.) harboring plasmid pBIN19::35S/BVLZ/NOST, described above. *A. tumefaciens* strain LBA4404 was maintained at a density of 5×10$^8$ cells/ml and was incubated with the tissue at room temperature for 30 min. The explants were blotted on sterile Whatman paper No. 1 and transferred to tobacco feeder plates. The cultures were incubated at 27° C. with 16 hr of light per day. After two days of incubation, the treated cotyledon segments were transferred to regeneration 2Z medium (Murashige and Skoog salt base with thiamine-HCl, 1.0 mg/l; pyridoxine-HCl, 0.5 mg/l; nicotinic acid, 0.5 mg/l; glycine, 2.0 mg/l; zeatin, 2.0 mg/l; sucrose, 30.0 g/l; myo-inositol, 100.0 mg/l, tissue culture agar, 8.0 g/l, pH 5.7) with 500 µg/ml cefotaxime and 100 µg/ml kanamycin. The cultures were incubated at 27° C. with 16 hours of light per day under 4,000 lux of light intensity.

D. Preparation of transgenic potato plants.

Potato tubers were obtained from potato plants of *Solanum tuberosum* cv. Desirée. Tubers that had been stored in the dark at 4° C. for one week were washed and rinsed with deionized water to remove soil, surface-sterilized one minute in 95% ethanol, and rinsed in sterile, distilled water. The tubers were peeled and disinfected for 15 minutes in 10% Purex (commercial bleach) containing two drops of Tween 20 per 100 ml solution followed by five rinses with sterile, distilled water. The proximal and distal quarter portions of the tubers were discarded. The sterilized potato tubers were immersed in MS liquid medium (Murashige and Skoog (1962), *Physiol. Plant* 15:473–496) for 20 min prior to removal of the discs.

The explants were floated in 20 mls of MS medium containing an overnight culture of *A. tumefaciens* strain LBA4404 (Clontech, Palo Alto, Calif.) harboring plasmid pBIN19::35S/BVLZ/NOST, described above, which had been pre-induced with 50 µM acetosyringone. The tissue and Agrobacterium were incubated at room temperature on a gyratory shaker with gentle shaking at approximately 60 rpm. After 20 minutes, the explants were blotted on sterile Whatman paper No. 1 and transferred to two-day-preconditioned tobacco feeder plates. Feeder plates were prepared according to the method of Horsch and Jones (*In Vitro* 16:103–108, 1980) with the following modification: cells from a six-day-old suspension culture were filtered through a sterile 30-mesh sieve, collected on two layers of sterile Kimwipes and freed of excess medium through a funnel. Cells were then resuspended in fresh MM medium to a final density of 0.3 g fresh-weight/ml. The suspension was stirred, and 1.5 ml aliquots were pipetted onto plates containing two kinds of shoot regeneration media, 3C52R medium and shoot initiation medium.

| Shoot Regeneration Medium 3C52R Medium | |
| --- | --- |
| Murashige and Skoog salt mixture | 4.3 g/L (GIBCO, Grand Island, NY) |

R3 vitamins:

| | |
|---|---|
| Thiamine.HCl | 1.0 mg/l |
| Nicotinic acid | 0.5 mg/l |
| Pyridoxine.HCl | 0.5 mg/l |
| Trans-Zeatin Riboside | 5 μM |
| Indole acetic acid.aspartic acid | 3 μM |
| Myo-inositol | 100.0 mg/l |
| Sucrose | 30.0 g/l |
| TC Agar | 8.0 g/l |
| pH 5.7 | |

Shoot initiation medium

Murashige and Skoog salt base

Nitsch vitamins:

| | |
|---|---|
| Thiamine.HCl | 0.1 mg/l |
| Nicotinic acid | 0.5 mg/l |
| Pyridoxine.HCl | 0.5 mg/l |
| Glycine | 2.0 mg/l |
| D-biotin | 0.05 mg/l |
| Folic acid | 0.5 mg/l |
| Gibberellic acid | 0.5 mg/l |
| 6-Benzylaminopurine | 3.0 mg/l |
| α-Naphthaleneacetic Acid | 0.03 g/l |
| Casein hydrolysate | 1.0 g/l |
| Myo-inositol | 100.0 mg/l |
| Sucrose | 30.0 g/l |
| TC Agar | 8.0 g/l |
| pH 5.7 | |

After two days, infected tuber discs were transferred to selection media containing cefotaxime (500 μg/ml) and kanamycin (100 μg/ml). The composition of the media is identical to incubation media, but there is no feeder layer. Tissues are transferred to fresh selection media at three-week intervals, and the cefotaxime concentration is reduced to 200 μg/ml after three weeks in culture. The cultures are incubated at 27° C. with 16 hours of light under 4000 lux light intensity throughout the experiments.

E. Preparation of transgenic rice plants.

Rice suspension cultures (*O. sativa* cv. Sasanishiki) are initiated from cells prepared according to the procedure of Kyozuka et al. ((1987) *Mol. Gen. Genet.* 206:408–413) starting with seeds obtained from the National Small Grains Collection, USDA. The suspension cultures are maintained and proliferated on N6 medium with 2.3 g/L L-proline.

The cultures are subcultured weekly. At each subculture, 2.5 gm fresh weight of rice suspension cells are transferred to 50 ml fresh medium. The cultures are incubated at 27° C. in the dark on a gyratory shaker at a speed of approximately 125 rpm.

Ten grams fresh weight of five-day-old suspension cells (*O. sativa* cv. Sasanishiki) are incubated in 100 ml Protoplast Wash Solution containing 1% Cellulase RS, 0.1% Pectolyase Y-23 (pH 6.0) at room temperature in the dark on a gyratory shaker at a speed of ~50 rpm for 4 hours.

The enzyme-protoplast mixture is passed through a 300 mesh tissue sieve to remove debris, then centrifuged at ~147×g for 10 minutes at room temperature. Pelleted protoplasts are washed twice by resuspending in ~35 ml Protoplast Wash Solution and centrifuging at ~147×g for 10 minutes after each resuspension. Protoplasts are purified by centrifugation through a Percoll Solution step gradient and then are resuspended in 6 ml of 70% Percoll Solution. Six ml of 50% Percoll Solution is layered on top of the resuspended protoplasts, and 6 ml of a 25% Percoll Solution is layered on top of the 50% Percoll Solution.

N6 medium

| Constituent | Concentration (mg/l) |
|---|---|
| $KNO_3$ | 2,830.0 |
| $(NH_4)_2SO_4$ | 463 |
| $KH_2PO_4$ | 400 |
| $MgSO_4.7H_2O$ | 185 |
| $CaCl_2.2H_2O$ | 166 |
| $Na_2.EDTA$ | 37.25 |
| $FeSO_4.7H_2O$ | 27.25 |
| KI | 0.8 |
| $H_3BO_3$ | 1.6 |
| $ZnSO_4.7H_2O$ | 1.5 |
| $MnSO_4.H_2O$ | 3.3 |
| Thiamine.HCl | 0.1 |
| Pyridoxine.HCl | 0.5 |
| Nicotinic acid | 0.5 |
| Glycine | 2.0 |
| 2,4-Dichlorophenoxyacetic acid | 2.0 |
| L-Tryptophan | 50 |
| Myo-inositol | 100 |
| Sucrose | 30,000 |
| pH 5.8 | |

Protoplast Wash Solution

| Constituent | Concentration (mg/l) |
|---|---|
| $KH_2PO_4$ | 27.2 |
| $KNO_3$ | 101.0 |
| $CaCl_2.2H_2O$ | 1.48 |
| $MgSO_4.7H_2O$ | 246.0 |
| KI | 0.16 |
| $CuSO_4.7H_2O$ | 0.025 |
| MES | 5 (mM) |
| Mannitol | 72.9 |
| pH 5.8 | |

PERCOLL Solution

| | | | |
|---|---|---|---|
| (1) | 70% Percoll Solution: | | |
| | Percoll Solution | 70.0 | ml/100 ml |
| | Commercial Murashige and Skoog Salt base | 0.43 | g/100 ml |
| | Sucrose | 3.0 | g/100 ml |
| (2) | 50% Percoll Solution: | | |
| | Percoll Solution | 50.0 | ml/100 ml |
| | Commercial Murashige and Skoog Salt base | 0.43 | g/100 ml |
| | Sucrose | 3.0 | g/100 ml |
| (3) | 25% Percoll Solution: | | |
| | Percoll Solution | 25 | ml/100 ml |
| | Commercial Murashige and Skoog Salt base | 0.43 | g/100 ml |
| | Sucrose | 3.0 | g/100 ml |

The Percoll-protoplast gradient is centrifuged at ~297×g for 15 minutes at room temperature. Protoplasts are collected at the interface of the 25% and 50% Percoll solutions using a sterile pasteur pipet and transferred to 25 ml of Protoplast Wash Solution. Protoplasts are washed twice by resuspending in 25 ml Protoplast Wash Solution and centrifuging at ~147×g for 10 minutes after each resuspension. The protoplasts are resuspended in Protoplast Wash Solution to a density of ~1×$10^7$ protoplasts per ml for transformation.

One-milliliter aliquots of protoplasts are separately mixed with 100 μg/ml plasmid DNA from a plasmid that contains cDNA encoding bovine lysozyme precursor. An equal volume of polyethylene glycol (PEG 8000, 40% w/v) in Krens' F solution (see, e.g., Krens et al. (1986) *Nature* 296:72–74), is added to the mixtures of protoplasts and plasmid DNAs. The protoplast-PEG mixture is heat shocked at 45° C. for 5 minutes followed by chilling on ice for 20 seconds. The solution is then brought to room temperature followed by incubation at 30° C. for 30 minutes and then is diluted with Krens' F solution until the PEG concentration is less than 2% according to the following time schedule as a reference:

| | |
|---|---|
| 0–2 min | two drops every 30 sec |
| 2–5 min | five drops every 30 sec |
| 5–10 min | 0.5 ml every 30 sec |
| 10–15 min | 1 ml every 30 sec |
| 15–30 min | 2 ml every 5 min |

The protoplasts treated with plasmid DNA are collected by centrifugation at approximately 147×g for 10 minutes, resuspended in $N_6$ medium containing 0.3M mannitol and incubated in the dark at room temperature on a gyratory shaker at ~50 rpm.

Protoplasts are then cultured using the method of Shillito et al. ((1983) *Plant Cell Rep.* 2:244–247). Two ml of protoplast suspension are mixed with equal amounts of rice protoplast medium (see, below), containing 2.5% Sea Plaque agarose and transferred to a petri dish.

Rice Protoplast Medium

| Constituent | Concentration (mg/l) |
|---|---|
| $KNO_3$ | 4,044.00 |
| $NaH_2PO_4.H_2O$ | 275.98 |
| $(NH_4)_2SO_4$ | 330.25 |
| $MgSO_4.7H_2O$ | 246.48 |
| $CaCl_2.2H_2O$ | 147.02 |
| $MnSO_4$ | 1.54 |
| $ZnSO_4.7H_2O$ | 2.20 |
| $H_3BO_3$ | 2.86 |
| $CuSO_4.5H_2O$ | 0.196 |
| $Na_2MoO_4.2H_2O$ | 0.11 |
| $FeSO_4.7H_2O$ | 10.24 |
| $Na_2.EDTA$ | 7.25 |
| Thiamine.HCl | 0.1 |
| Pyridoxine.HCl | 0.5 |
| Nicotinic acid | 0.5 |
| Glycine | 2.0 |
| 2,4-Dichlorophenoxyacetic acid | 2.0 |
| Myo-inositol | 100 |
| Sucrose | 0.4(M) |
| pH 5.6 | |

The solidified agar containing the protoplasts is cut into 4 mm blocks and transferred to a 6 cm petri dish containing 5 ml of protoplast medium and about 100 mg of 5-day-old *O. sativa* cv. Sasanishiki suspension cells (the nurse cells). The cultures are incubated at 25° C. in the dark on a gryratory shaker at about 40 rpm. Rice plants are regenerated from protoplasts as described by Kyozuka et al. ((1987) *Mol. Gen. Genet.* 206:408–413).

EXAMPLE 5

Greenhouse tomato plants exposed to *Pseudomonas syringae* pv. *tomato* and then treated with bovine lysozyme exhibited fewer lesions than untreated plants.

Tomato plants were exposed to *Pseudomonas syringae* pv. *tomato* and then treated with bovine lysozyme, which had been produced by *P. pastoris* and purified from the broth. Following treatment, the number of lesions that developed on the treated plants were compared to the number that developed on untreated control plants.

The plants, which were four weeks old at the time of treatment, had been germinated in a greenhouse from seeds of two cultivars, El Presidente and Peto 86. Ten groups of seven plants per group were germinated from the El Presidente seeds (groups A–J), and ten groups of seven plants from the Peto 86 seeds (groups K–Q/R and S–U) were, except for G and Q/R, first sprayed with 10 mls of $1\times10^7$ cfu *P. syringae* per ml in water, allowed to dry and then treated as follows:

TABLE 2

| Group | Treatment |
|---|---|
| A and K | sprayed with 0.1M $NaPO_4$, pH 5 |
| B and L | sprayed with 125 ppm lysozyme in 0.1M $NaPO_4$, pH 5 |
| C and M | sprayed with 250 ppm lysozyme in 0.1M $NaPO_4$, pH 5 |
| D and N | sprayed with 500 ppm lysozyme in 0.1M $NaPO_4$, pH 5 |
| E and O | sprayed with $CuSO_4$ in $H_2O$ (3 tsp/gal) |
| F and P | sprayed with 250 ppm lysozyme in 0.1M $NaPO_4$, pH 5 + $CuSO_4$ in $H_2O$ (3 tsp/gal) |
| G and Q/R | Untreated |
| H and S | sprayed with 250 ppm lysozyme in 0.1M $NaPO_4$ |
| I and T | no further treatment |

Seven days after the initial treatment, the treatments were repeated. After an additional seven days, the leaflets from the third true leaf from the bottom of each plant were removed, and the number of lesions/leaflet were counted. The mean number of lesions/leaf were compared.

Untreated plants and plants sprayed with lysozyme or $CuSO_4$ only, did not develop lesions. All plants that were exposed to bacteria developed detectable lesions. Except for the Peto 86 plants treated with 250 ppm, plants that had been exposed to the bacteria and treated with lysozyme had fewer lesions than those exposed to bacteria in the absence of lysozyme.

The effects of $CuSO_4$ on the susceptibility of the two cultivars to infection varied. The El Presidente plants that were exposed to bacteria and either treated with $CuSO_4$ alone or in combination with lysozyme, developed at least the same number of lesions as the untreated exposed plants. In contrast, Peto 86 plants treated with $CuSO_4$ alone or in combination with lysozyme, and exposed to the bacteria, developed fewer lesions than untreated plants that had been exposed to the bacteria.

The experiment was repeated using El Presidente tomato plants. As above, the bacteria were sprayed onto the plants. After drying, the plants were treated with lysozyme. Each treatment was repeated 7 times.

TABLE 3

| | Total No. Lesions | | | | | | |
|---|---|---|---|---|---|---|---|
| Treatment* | A | B | C | D | E | F | G |
| 3RD Branch | 1079 | 664 | 1617 | 672 | 434 | 0 | 0 |
| 4TH Branch | 601 | 265 | 1039 | 149 | 174 | 0 | 0 |
| TOTAL | 1680 | 929 | 2656 | 821 | 608 | 0 | 0 |

*A Bacteria only
B Bacteria, dry, then buffer
C Bacteria, dry; then buffer + 125 ppm bovine lysozyme c2

TABLE 3-continued

Total No. Lesions

| Treatment* | A | B | C | D | E | F | G |
|---|---|---|---|---|---|---|---|

D Bacteria, dry, then buffer + 250 ppm bovine lysozyme c2
E Bacteria, dry, then buffer + 500 ppm bovine lysozyme c2
F 250 ppm bovine lysozyme c2
G No treatment

TABLE 4

Total No. Lesions/cm²

| Treatment* | A | B | C | D | E | F | G |
|---|---|---|---|---|---|---|---|
| 3RD Branch | 1.44 | 1.01 | 2.13 | 1.15 | 0.57 | 0.00 | 0.00 |
| 4TH Branch | 0.80 | 0.40 | 1.41 | 0.26 | 0.29 | 0.00 | 0.00 |
| TOTAL | 1.12 | 0.70 | 1.77 | 0.70 | 0.43 | 0.00 | 0.00 |

*A Bacteria only
B Bacteria, dry, then buffer
C Bacteria, dry, then buffer + 125 ppm bovine lysozyme c2
D Bacteria, dry, then buffer + 250 ppm bovine lysozyme c2
E Bacteria, dry, then buffer + 500 ppm bovine lysozyme c2
F 250 ppm bovine lysozyme c2
G No treatment

EXAMPLE 6

Transgenic tobacco plants that express bovine lysozyme c were less susceptible to bacterial infection than plants that do not express bovine lysozyme c2.

Four transgenic tobacco plants that express bovine lysozyme c2 were transferred from tissue culture to soil and maintained in a growth chamber. Two untransformed tobacco plants, and one plant that expressed the GUS gene under the control of the CaMV 35S promoter, were also transferred into soil in the growth chamber.

Three weeks after transfer to soil, each plant was sprayed with 25 ml of water that contained $1 \times 10^7$ cfu/ml *Pseudomonas syringae* pv. *tabacci*. Two weeks after exposure to the bacteria, the number of lesions on leaves that had been contacted with the spray were counted.

The results, showing the numbers of lesions on the four transgenic plants that express bovine lysozyme c2 and the three control plants, are set forth in Table 5.

TABLE 5

| Plant | Total No. lesions | No. leaves contacted | No. lesions per leaf |
|---|---|---|---|
| Untransformed | 196 | 8 | 24.5 |
| Untransformed | 246 | 8 | 30.8 |
| Transformed CaMV 35S-GUS | 72 | 8 | 7.2 |
| Transformed #1 CaMV 35S-lysozyme | 13 | 10 | 1.5 |
| Transformed #2 CaMV 35S-lysozyme | 3 | 9 | 3 |
| Transformed #3 CaMV 35S-lysozyme | 63 | 8 | 7.8 |
| Transformed #4 CaMV 35S-lysozyme | 168 | 3 | 56 |

Three of the four plants that expressed bovine lysozyme c2 (transformant Nos. 1–3) developed substantially fewer lesions than the two untransformed plants.

EXAMPLE 7

Tuber challenge inoculations were conducted with *Erwinia carotovora carotovora* (Ecc). Transgenic lines were made of the cultivars '1533' and '795'. The data set include non-inoculated cultivars of these parent cultivars as controls.

Potatoes were inoculated with 20 μl of a 1:2 dilution of a 0.1 OD 620 nm bacterial suspension of *Erwinia carotovora carotovora* as follows:

One 15 mm deep hole was punched in each tuber, filled with 20 μl suspension immediately, then sealed with Vaseline. Potatoes were placed on test tube racks in plastic boxes lined with wet paper towels. A small amount of free standing water was allowed in the bottom of the box for wicking. 22 potatoes could be accommodated in each box, so 22 lines were evaluated, including 1533 and 795 controls, with one tuber from each line in each of 8 boxes to make 8 repetitions. Potatoes were incubated at 25° C. for 24 hours before taking fresh weight of rot.

TABLE 6

FRESH WEIGHT OF ROT (gm)

| Line # | Rep 1 | Rep 2 | Rep 3 | Rep 4 | Rep 5 | Rep 6 | Rep 7 | Rep 8 | Ave. | tDe |
|---|---|---|---|---|---|---|---|---|---|---|
| 1533* | 1.74 | 0.54 | 1.05 | 1.53 | 0.83 | 0.85 | 0.87 | 0.95 | 1.05 | 0.40 |
| 4654 | 0.56 | 0.66 | 0.46 | 0.55 | 0.5 | 0.56 | 0.51 | 0.55 | 0.54 | 0.06 |
| 5026 | 0.42 | 0.5 | 0.4 | 0.4 | 0.38 | 0.41 | 0.39 | 0.62 | 0.44 | 0.08 |
| 5027 | 0.61 | 0.64 | 0.78 | 0.59 | 0.53 | 0.63 | 0.49 | 0.65 | 0.62 | 0.09 |
| 5032 | 0.34 | 0.68 | 0.38 | 0.54 | 0.52 | 0.45 | 0.46 | 0.47 | 0.48 | 0.10 |
| 5035 | 0.52 | 0.67 | 0.67 | 0.57 | 0.71 | 0.47 | 0.4 | 0.4 | 0.55 | 0.12 |
| 5037 | 0.72 | 0.97 | 0.51 | 0.45 | 0.71 | 0.61 | 0.36 | 0.55 | 0.61 | 0.19 |
| 5038 | 0.62 | 0.55 | 1.91 | 0.6 | 0.61 | 0.46 | 0.39 | 0.58 | 0.72 | 0.49 |
| 5043 | 0.35 | 0.69 | 0.92 | 0.66 | 0.64 | 0.95 | 0.65 | 0.58 | 0.68 | 0.19 |
| 5406 | 0.55 | 0.44 | 0.63 | 0.55 | 0.69 | 0.51 | 0.36 | 0.64 | 0.55 | 0.11 |
| 5464 | 0.53 | 0.53 | 0.47 | 0.6 | 0.65 | 0.53 | 0.4 | 0.5 | 0.53 | 0.08 |
| 5465 | 0.33 | 0.61 | 0.56 | 0.69 | 0.5 | 0.63 | 0.48 | 0.52 | 0.54 | 0.11 |

*= uninoculated control
tDe = calculated Student's T deviation

TABLE 7

FRESH WEIGHT OF ROT (gm)

| Line # | Rep 1 | Rep 2 | Rep 3 | Rep 4 | Rep 5 | Rep 6 | Rep 7 | Rep 8 | Ave. | tDe |
|---|---|---|---|---|---|---|---|---|---|---|
| 1533* | 0.48 | 0.46 | 0.41 | 0.58 | 0.54 | 0.42 | 0.57 | 0.54 | 0.50 | 0.07 |
| 4889 | 0.43 | 0.38 | 0.31 | 0.5 | 0.51 | 0.4 | 0.4 | 0.61 | 0.44 | 0.09 |
| 4976 | 0.39 | 0.33 | 0.39 | 0.6 | 0.3 | 0.64 | 0.65 | 0.75 | 0.51 | 0.17 |
| 4982 | 0.37 | 0.31 | 0.45 | 0.29 | 0.03 | 0.31 | 0.37 | 0.53 | 0.33 | 0.15 |
| 4985 | 0.26 | 0.34 | 0.36 | 0.37 | 0.37 | 0.45 | 0.25 | 0.37 | 0.35 | 0.06 |
| 5007 | 0.34 | 0.38 | 0.47 | 0.55 | 0.29 | 0.38 | 0.59 | 0.36 | 0.42 | 0.11 |
| 5011 | 0.33 | 0.36 | 0.41 | 0.47 | 0.43 | 0.6 | 0.51 | 0.52 | 0.45 | 0.09 |
| 5033 | 0.28 | 0.35 | 0.68 | 0.37 | 0.29 | 0.44 | 0.43 | 0.57 | 0.43 | 0.14 |
| 5381 | 0.73 | 0.37 | 0.56 | 0.43 | 0.34 | 0.35 | 0.34 | 0.51 | 0.45 | 0.14 |
| 5405 | 0.45 | 0.34 | 0.32 | 0.31 | 0.37 | 0.32 | 0.51 | 0.5 | 0.39 | 0.08 |
| 5408 | 0.3 | 0.29 | 0.44 | 0.36 | 0.44 | 0.35 | 0.39 | 0.34 | 0.36 | 0.06 |
| 5409 | 0.34 | 0.55 | 0.41 | 0.57 | 0.38 | 0.46 | 0.41 | 0.36 | 0.44 | 0.09 |
| 5413 | 0.46 | 0.1 | 0.41 | 0.36 | 0.25 | 0.61 | 0.49 | 0.26 | 0.37 | 0.16 |
| 5416 | 0.49 | 0.38 | 0.53 | 0.45 | 0.33 | 0.45 | 0.52 | 0.45 | 0.45 | 0.07 |
| 5417 | 0.29 | 0.44 | 0.42 | 0.55 | 0.46 | 0.71 | 0.41 | 0.6 | 0.49 | 0.13 |
| 5419 | 0.31 | 0.33 | 0.42 | 0.45 | 0.37 | 0.32 | 0.37 | 0.32 | 0.36 | 0.05 |
| 5462 | 0.43 | 0.44 | 0.32 | 0.42 | 0.5 | 0.38 | 0.36 | 0.39 | 0.41 | 0.06 |

*= uninoculated control
tDe = calculated Student's T deviation

TABLE 8

FRESH WEIGHT OF ROT (gm)

| Line # | Rep 1 | Rep 2 | Rep 3 | Rep 4 | Rep 5 | Rep 6 | Rep 7 | Rep 8 | Ave. | tDe |
|---|---|---|---|---|---|---|---|---|---|---|
| 795* | 0.45 | 0.45 | 0.36 | 0.43 | 0.42 | 0.46 | 0.57 | 0.48 | 0.45 | 0.06 |
| 4000 | 0.49 | 0.45 | 0.38 | 0.45 | 0.47 | 0.4 | 0.34 | 0.51 | 0.44 | 0.06 |
| 4003 | 0.32 | 0.41 | 0.51 | 0.33 | 0.31 | 0.59 | 0.29 | 0.39 | 0.39 | 0.11 |
| 4004 | 0.42 | 0.44 | 0.42 | 1.86 | 0.36 | 0.41 | 0.44 | 0.68 | 0.63 | 0.51 |
| 4813 | 0.41 | 0.57 | 0.48 | 0.41 | 0.42 | 0.5 | 0.48 | 0.49 | 0.47 | 0.06 |
| 5373 | 0.52 | 0.31 | 0.37 | 0.42 | 0.28 | 0.55 | 0.76 | 0.28 | 0.44 | 0.17 |
| 5376 | 0.38 | 0.37 | 0.45 | 0.36 | 0.37 | 0.56 | 0.4 | 0.33 | 0.40 | 0.07 |

*= uninoculated control
tDe = calculated Student's T deviation

The data in Tables 6–8 above show resistance to the microbial challenge by Ecc provided in plant transformants that express bovine lysozyme C.

Since modifications will be apparent to those of skill in the art, it is intended that this invention be limited only by the scope of the appended claims.

---

We claim:

1. A transgenic plant that is resistant to plant pathogens, comprising heterologous DNA encoding a ruminant or ruminant-like lysozyme, wherein the plant expresses sufficient levels of the lysozyme to render it less susceptible to said pathogens than the wild-type plant, which is susceptible to said pathogens and which does not express the lysozyme.

2. The transgenic plant of claim 1, wherein the transgenic plant is rendered resistant to at least one of said pathogens.

3. The transgenic plant of claim 1, wherein said pathogens are selected from the group consisting of Pseudomonas, Erwinia, Agrobacteria, Xanthomonas, and Clavibacter.

4. The transgenic plant of claim 1, wherein said pathogens are selected from the group consisting of *Agrobacterium tumefaciens, Pseudomonas tolaasii, Pseudomonas solanacearum, Pseudomonas syringae, Xanthomonas campestris* and *Erwinia carotovora*.

5. The transgenic plant of claim 1, wherein said plant is a dicotyledonous plant.

6. The transgenic plant of claim 1, wherein said plant is a monocotyledonous plant.

7. The transgenic plant of claim 1, wherein said plant is a potato, tomato, rice or tobacco plant.

8. The transgenic plant of claim 1, wherein said lysozyme is a bovine lysozyme c.

9. Plant cells, comprising heterologous DNA encoding a ruminant or ruminant-like lysozyme.

10. The plant cells of claim 9, wherein said lysozyme is a bovine lysozyme c.

11. Plant protoplasts, comprising heterologous DNA encoding a ruminant or ruminant-like lysozyme.

12. The plant protoplasts of claim 11, wherein said lysozyme is a bovine lysozyme c.

13. Seeds produced from the transgenic plant of claim 1, wherein said seeds contain heterologous DNA encoding a ruminant or ruminant-like lysozyme.

14. The seeds of claim 13, wherein said lysozyme is bovine lysozyme c.

15. A method for producing a ruminant or ruminant-like lysozyme, comprising:

cultivating a transgenic plant that expresses heterologous DNA that encodes the ruminant or ruminant-like lysozyme; and isolating the ruminant or ruminant-like lysozyme from the tissues of the plant.

16. The method of claim 15, wherein said lysozyme is a bovine lysozyme c.

17. The transgenic plant of claim 1, wherein the DNA encoding the lysozyme comprises a sequence of nucleotides that encodes a signal peptide that directs transport of the encoded lysozyme through the processing pathway of the plant, whereby the mature protein is produced.

18. The transgenic plant of claim 17, wherein the encoded signal peptide comprises amino acids that have the sequence set forth in sequence ID No. 3.

* * * * *